(12) United States Patent
Chen

(10) Patent No.: US 8,664,244 B2
(45) Date of Patent: Mar. 4, 2014

(54) COMPOUNDS AS C-MET KINASE INHIBITORS

(75) Inventor: Guoqing Paul Chen, Moorpark, CA (US)

(73) Assignee: Advenchen Pharmaceuticals, LLC, Moorpark, CA (US)

( * ) Notice: Subject to any disclaimer, the term of this patent is extended or adjusted under 35 U.S.C. 154(b) by 122 days.

(21) Appl. No.: 13/227,866

(22) Filed: Sep. 8, 2011

(65) Prior Publication Data

US 2012/0123126 A1     May 17, 2012

Related U.S. Application Data

(60) Provisional application No. 61/381,995, filed on Sep. 12, 2010.

(51) Int. Cl.
*A61K 31/04* (2006.01)
*C07D 215/38* (2006.01)

(52) U.S. Cl.
USPC .......................... 514/312; 546/159

(58) Field of Classification Search
USPC .......................... 546/159; 514/312
See application file for complete search history.

(56) References Cited

PUBLICATIONS

Grivennikov, Cell, Mar. 19, 2010, vol. 140(6), pp. 883-899.*
Raghav, 2012, Clin Cancer Res, vol. 18, pp. 2269, abstract.*
Tu, BNC Cancer, vol. 10(556), pp. 1-10, 2010.*

* cited by examiner

*Primary Examiner* — D M Seaman

(57) ABSTRACT

The present invention relates to compounds, processes for their preparation, pharmaceutical compositions containing them as active ingredient, methods for the treatment of disease states associated with the inhibition of the protein tyrosine kinase activity of growth factor receptors such as c-Met, thereby making them useful as anticancer agents, to their use as medicaments for use in the production of inhibition of tyrosine kinases reducing effects in warm-blooded animals such as humans.

Formula I

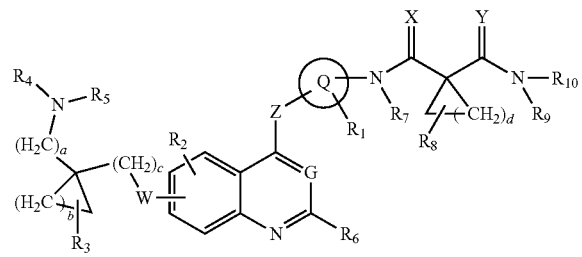

7 Claims, No Drawings

COMPOUNDS AS C-MET KINASE INHIBITORS

This application claims the benefit of U.S. Provisional Application No. 61/381,995 filed on Sep. 12, 2010.

FIELD OF THE INVENTION

The present invention relates to compounds, processes for their preparation, pharmaceutical compositions containing them as active ingredient, methods for the treatment of disease states associated with the inhibition of the protein tyrosine kinase activity of growth factor receptors such as c-Met, thereby making them useful as anticancer agents, to their use as medicaments for use in the production of inhibition of tyrosine kinases reducing effects in warm-blooded animals such as humans.

BACKGROUND OF THE INVENTION

Receptor tyrosine kinases are large enzymes that span the cell membrane and possess an extracellular binding domain for growth factors, a transmembrane domain, and an intracellular portion that functions as a kinase to phosphorylate a specific tyrosine residue in proteins and hence to influence cell proliferation. Tyrosine kinases may be classified as growth factor receptor (e.g. EGFR, PDGFR, FGFR and erbB2) or non-receptor (e.g. c-src and bcr-abl) kinases. Such kinases may be aberrantly expressed in common human cancers such as breast cancer, gastrointestinal cancers such as colon, rectal or stomach cancer, leukemia, and ovarian, bronchial or pancreatic cancer. Aberrant erbB2 activity has been implicated in breast, ovarian, non-small cell lung, pancreatic, gastric and colon cancers.

The kinase, c-Met, is the prototypic member of a subfamily of heterodimeric receptor tyrosine kinases (RTKs) which include Met, Ron and Sea. The antiangiogenic and antiproliferative activity of c-Met becomes a attractive target. The endogenous ligand for c-Met is hepatocyte growth factor (HGF), also known as scatter factor (SF), because of its ability to disrupt colony formation in vitro. HGF is a derived cytokine known to induce activation of the receptor via autophosphorylation resulting in an increase of receptor dependent signaling in normal and neoplastic cells (Sonnenberg et al., J. Cell Biol. 123:223-235, 1993; Matsumato et al, Crit. Rev. Oncog. 3:27-54, 1992; and Stoker et al., Nature 327:239-242, 1987). Anti-HGF antibodies or HGF antagonists also have been shown the inhibition of tumor metastasis.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma. Tumor angiogenesis, the formation of new blood vessels and their permeability is primarily regulated by (tumor-derived) vascular endothelial growth factor (VEGF), which acts via at least two different receptors: VEGF-R1 (Flt-1); and VEGF-R2 (KDR, Flk-1). The VEGF KDR receptor is highly specific for vascular endothelial cells (Endocr. Rev. 1992, 13, 18; FASEB J. 1999, 13, 9).

The present invention is based on the discovery of compounds that surprisingly inhibit the effect of c-Met and VEGF as well as other signal transduction of kinases, a property of value in the treatment of disease states associated with cell proliferation, angiogenesis and/or other signal transduction pathways, such as cancer, diabetes, psoriasis, rheumatoid arthritis, Kaposi's, haemangioma, acute and chronic nephropathies, atheroma, arterial restenosis, autoimmune disease, acute inflammation, excessive scar formation and adhesions, lymphoedema, endometriosis, dysfunctional uterine bleeding and ocular diseases with retinal vessel proliferation.

It has now been found that compounds of formula I, described below, are a new class of compounds that have advantageous pharmacological properties and inhibit the activity of protein tyrosine kinases, such as c-Met, VEGFr, EGFr, c-kit, PDGF, FGF, SRC, Ron, Tie2 etc. They may also be irreversible inhibitors of protein tyrosine kinases.

Examples of compounds that are similar in structure to those of the present invention are disclosed in the following literatures: WO2005117867, WO 2006108059, WO2007035428, WO2007054831, WO2008041053, WO2008112408, WO2010045095.

SUMMARY OF THE INVENTION

The present invention relates to the compounds of formula I

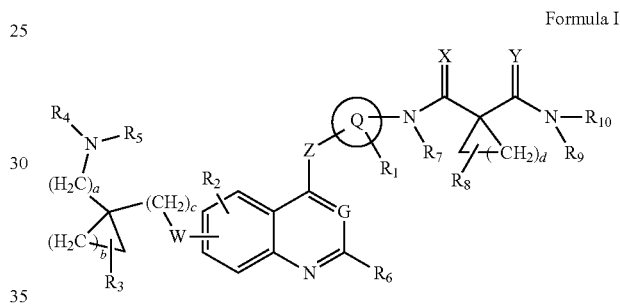

Formula I

Wherein
X and Y are each independently selected from O, S;
W and Z are each independently selected from O, S, N—R or CH—R;
G is selected from C—R, C—(CN) or N;
R is selected from H, halogen, halogeno-lower alkyl, lower alkyl, hydroxy, lower alkoxy, lower alkoxyalkoxy, lower alkenyl, lower alkynyl, amino, alkylamino, alkoxyamino, cycloalkyl, cycloalkenyl, aryl, lower alkylaryl, heterocyclyl or lower alkylheterocyclyl;
$R_1$, $R_2$, $R_3$ and $R_8$ are each independently selected from H, halogen, halogeno-lower alkyl, lower alkyl, hydroxy, lower alkoxy, lower alkoxyalkoxy, lower alkenyl, or lower alkynyl;
$R_4$, and $R_5$ are each independently selected from H, halogen, halogeno-lower alkyl, lower alkyl, cycloalkyl, lower alkyl cycloalkyl, cycloalkenyl, hydroxy, lower alkoxy, lower alkoxyalkoxy, lower alkenyl, lower alkynyl, aryl, lower alkylaryl, heterocyclyl, lower alkylheterocyclyl, lower alkyl-OC(=O)—, aryl-OC(=O)—, lower alkylaryl-OC(=O)—, heterocyclyl-OC(=O)—, lower alkylheterocyclyl-OC(=O)—, lower alkylenylaryl-OC(=O)—, lower alkyl-C(=O)—, aryl-C(=O)—, lower alkylenylaryl-C(=O)—, lower alkyl-$SO_2$—, ary-$SO_2$—, lower alkylenylaryl-$SO_2$—, lower alkyl-N(R)C(=O)—, aryl-N(R)C(=O)—, or lower alkylenylaryl-N(R)C(=O)—; $R_4$ and $R_5$ connect together to form a 3-8 membered saturated or unsaturated ring with their attached nitrogen;
$R_6$, $R_7$ and $R_9$ selected from H, halogeno-lower alkyl, lower alkyl;
$R_{10}$ is selected from H, halogen, halogeno-lower alkyl, lower alkyl, hydroxy, lower alkoxy, lower alkoxyalkoxy, lower alkenyl, lower alkynyl, amino, alkylamino, alkoxyamino, cycloalkyl, cycloalkenyl, aryl, lower alkylaryl, heterocyclyl or lower alklyheterocyclyl;

a and c are each independently selected from 0, 1, 2, 3 or 4;

b and d are each independently selected from 1, 2, 3, 4 or 5;

ring Q is a 5 to 13-membered monocyclic, bicyclic or tricyclic moiety which moiety may be saturated or unsaturated, which may be aromatic or non-aromatic, and which optionally may contain 1-3 heteroatoms selected independently from O, N and S;

or a pharmaceutically acceptable salt thereof.

DETAILED DESCRIPTION OF THE INVENTION

The present invention is directed to novel compounds which can inhibit protein tyrosine kinase, such as c-Met and VEGF, and use of these compounds for inhibition of c-Met or angiogenesis in the treatment of a neoplastic or proliferative or chronic inflammatory or angiogenic diseases which are caused by excessive or inappropriate angiogenesis in a mammal in need thereof.

In the compounds of formula (I),

X and Y are each independently selected from O, S; preferably X and Y are O;

W and Z are each independently selected from O, S, N—R or CH—R; preferably W and Z are selected from O or N—R;

G is selected from C—R, C—(CN) or N; preferably are selected from C—R or N;

R is selected from H, halogen, halogeno-lower alkyl, lower alkyl, hydroxy, lower alkoxy, lower alkoxyalkoxy, lower alkenyl, lower alkynyl, amino, alkylamino, alkoxyamino, cycloalkyl, cycloalkenyl, aryl, lower alkylaryl, heterocyclyl or lower alkylheterocyclyl; preferably are selected from H, halogen, halogeno-lower alkyl, lower alkyl;

$R_1$, $R_2$, $R_3$ and $R_8$ are each independently selected from H, halogen, halogeno-lower alkyl, lower alkyl, hydroxy, lower alkoxy, lower alkoxyalkoxy, lower alkenyl, or lower alkynyl; preferably are selected from H, halogen, halogeno-lower alkyl, lower alkyl, hydroxy, lower alkoxy, lower alkoxyalkoxy;

$R_4$, and $R_5$ are each independently selected from H, halogen, halogeno-lower alkyl, lower alkyl, cycloalkyl, lower alkyl cycloalkyl, cycloalkenyl, hydroxy, lower alkoxy, lower alkoxyalkoxy, lower alkenyl, lower alkynyl, aryl, lower alkylaryl, heterocyclyl, lower alkylheterocyclyl, lower alkyl-OC(=O)—, aryl-OC(=O)—, lower alkylaryl-OC(=O)—, heterocyclyl-OC(=O)—, lower alkylheterocyclyl-OC(=O)—, lower alkylenylaryl-OC(=O)—, lower alkyl-C(=O)—, aryl-C(=O)—, lower alkylenylaryl-C(=O)—, lower alkyl-SO$_2$—, ary-SO$_2$—, lower alkylenylaryl-SO$_2$—, lower alkyl-N(R)C(=O)—, aryl-N(R)C(=O)—, or lower alkylenylaryl-N(R)C(=O)—; preferably selected from H, halogeno-lower alkyl, lower alkyl, cycloalkyl, lower alkyl cycloalkyl, lower alkoxy, lower alkyl-OC(=O)—, aryl-OC(=O)—, lower alkylaryl-OC(=O)—, heterocyclyl-OC(=O)—, lower alkylheterocyclyl-OC(=O)—, lower alkylenylaryl-OC(=O)—;

$R_4$ and $R_5$ connect together to form a 3-8 membered saturated or unsaturated ring with their attached nitrogen; preferably $R_4$ and $R_5$ connect together to form a cycloalkyl or heterocyclyl;

$R_6$, $R_7$ and $R_9$ are selected from H, halogeno-lower alkyl, lower alkyl; preferably is H;

$R_{10}$ is selected from H, halogen, halogeno-lower alkyl, lower alkyl, hydroxy, lower alkoxy, lower alkoxyalkoxy, lower alkenyl, lower alkynyl, amino, alkylamino, alkoxyamino, cycloalkyl, cycloalkenyl, aryl, lower alkylaryl, heterocyclyl or lower alklyheterocyclyl; preferably is an aryl and further preferred is selected from a phenyl, substituted phenyl, or a heterocyclyl;

a and c are each independently selected from 0, 1, 2, 3 or 4; preferably are selected from 0, 1 or 2;

b and d are each independently selected from 1, 2, 3, 4 or 5; preferably are selected from 1, 2 or 3;

ring Q is a 5 to 13-membered monocyclic, bicyclic or tricyclic moiety which moiety may be saturated or unsaturated, which may be aromatic or non-aromatic, and which optionally may contain 1-3 heteroatoms selected independently from O, N and S; preferably ring Q is an aryl and further preferred is selected from a phenyl or a substituted phenyl; or ring Q is a 5-6-membered heteroaromatic moiety which contains 1-3 heteroatoms selected independently from O, N and S, preferably is a pyridine;

or a pharmaceutically acceptable salt thereof.

The term "halogen", as used herein, unless otherwise indicated, includes fluoro, chloro, bromo or iodo. such as fluoro and chloro.

The term "halogen-lower alkyl", as used herein, unless otherwise indicated, includes 1 to 6 halogen substituted alkyl, such as trifluoromethyl.

The term "lower alkyl", as used herein, unless otherwise indicated, includes 1 to 6 saturated monovalent hydrocarbon radicals having straight or branched moieties, including, but not limited to, methyl, ethyl, n-propyl, iso-propyl, n-butyl, sec-butyl, tert-butyl, and the like.

The term "lower alkenyl", as used herein, unless otherwise indicated, includes lower alkyl groups, as defined above, having at least one carbon-carbon double bond, such as —CH$_2$—CH=CH$_2$.

The term "lower alkynyl", as used herein, unless otherwise indicated, includes lower alkyl groups, as defined above, having at least one carbon-carbon triple bond, such as —CH$_2$—C≡CH.

The term "lower alkoxy", as used herein, unless otherwise indicated, includes —O-lower alkyl groups wherein lower alkyl is as defined above, such as methoxy and ethoxy.

The term "lower alkoxyalkoxy", as used herein, unless otherwise indicated, includes —O-lower alkyl-O-lower alkyl groups wherein lower alkyl is as defined above, such as —OCH$_2$CH$_2$OCH$_3$.

The term "lower alkylenyl", as used herein, unless otherwise indicated, includes 1 to 6 saturated —CH$_2$— radicals.

The term "amino", as used herein, unless otherwise indicated, includes —NH$_2$ group, —NH-lower alkyl group, or —N(lower alkyl)$_2$ group wherein lower alkyl is as defined above, such as methylamino and dimethylamino.

The term "alkyamino", as used herein, unless otherwise indicated, includes -lower alkyl-NH$_2$ group, -lower alkyl-NH-lower alkyl group, or -lower alkyl-N(lower alkyl)$_2$ group wherein lower alkyl is as defined above, such as —CH$_2$CH$_2$NHCH$_3$.

The term "alkoxyamino", as used herein, unless otherwise indicated, includes —O-lower alkyl-NH$_2$ group, —O-lower alkyl-NH-lower alkyl group, or —O-lower alkyl-N(lower alkyl)$_2$ group wherein lower alkyl is as defined above, such as —OCH$_2$CH$_2$NHCH$_3$.

The term "aryl", as used herein, unless otherwise indicated, includes an organic radical derived from an aromatic hydrocarbon by removal of one hydrogen, such as phenyl or naphthyl, preferably phenyl, and is unsubstituted or substituted by one or two substituents, selected from halogen, halogeno-lower alkyl, lower alkyl, lower alkenyl, lower alkynyl, cyano, lower alkylcyano, hydroxy, lower alkoxy, carboxy, carboxyalkyl, amino, carbamoyl, cabamate, ureido, mercapto, sulfo, lower alkysulfinyl, lower alkanesulfonyl, sulfonamide; aryl includes one aromatic ring fused with an aliphatic ring, such as a saturated or partially saturated ring, such as tetrahydronaphthyl.

The term "heterocyclyl", as used herein, unless otherwise indicated, includes non-aromatic saturated or partial saturated single and fused rings suitably containing up to four heteroatoms in each ring, each of which independently selected from O, N and S, and which rings, may be unsubstituted or substituted independently by, for example, up to three substituents. Each heterocyclic ring suitably has from 4 to 7, preferably 5 or 6, ring atoms. A fused heterocyclic ring system may include carbocyclic rings and need include only one heterocyclic ring which may be partially saturated or saturated. The heterocyclyl includes mono, bicyclic and tricyclic heteroaromatic ring systems comprising up to four, preferably 1 or 2, heteroatoms each selected from O, N and S. Each ring may have from 4 to 7, preferably 5 or 6, ring atoms. A bicyclic or tricyclic ring system may include a carbocyclic ring. Carbocyclic ring includes cycloalkyl, cycloalkenyl or aryl ring. examples of heterocyclyl groups include but not limited: azetidine, pyrrolidine, pyrrolidione, piperidine, piperidinone, piperazine, morpholine, oxetane, tetrahydrofuran, tetrahydropyran, imidazolidine, pyrazolidine and hydantoin, pyrrole, indole, pyrazole, indazole, trizole, benzotrizole, imidazole, benzoimdazole, thiophene, benzothiophene, thiozole, benzothiozole, furan, benzofuran, oxazole, bezoxazole, isoxazole, tetrazole, pyridine, pyrimidine, trizine, quinoline, isoquinoline, quinazoline, indoline, indolinone, benzotetrahydrofuran, tetrahydroquinoline, tetrahydroisoquinoline, methylene-dioxyphenyl. The heterocyclic and heterocyclic rings may be optionally substituted and substituents selected from the group defined above as substituents for aryl.

The term "cycloalkyl", as used herein, unless otherwise indicated, includes cyclic radicals having from three to eight ring carbon atoms, including, but not limited to cyclopropyl, cyclobutyl, cyclopentyl, cyclohexyl, and the like. The cycloalkyl groups may be optionally substituted one or more times, substituents selected from the group defined above as substituents for aryl, preferably halogen, lower alkyl.

The term "lower alkyl cycloalkyl", as used herein, unless otherwise indicated, includes -lower alkyl-cycloalkyl group wherein lower alkyl and cycloalkyl are as defined above.

The term "cycloalkenyl", as used herein, unless otherwise indicated, includes cycloalkyl groups, as defined above, having at least one carbon-carbon double bond.

The term "lower alkylaryl", as used herein, unless otherwise indicated, includes—lower alkyl-aryl group wherein lower alkyl and aryl are as defined above.

The term "lower alkylheterocyclyl", as used herein, unless otherwise indicated, includes—lower alkyl-heterocyclyl group wherein lower alkyl and heterocyclyl are as defined above.

The term "lower alkylenylaryl", as used herein, unless otherwise indicated, includes—lower alkylenyl aryl group wherein aryl and lower alkylenyl are as defined above.

Most in vitro tyrosine kinase inhibition activities can be tested with Millipore Ltd in their kinases panel screening.

Compounds listed in examples have the following inhibition activities towards c-Met and some tumor cell lines.

| Example | c-Met Inhibition % Activity (0.3 μM) | SHG44 IC50 μM | A549 IC50 μM | PC-3M IC50 μM |
| --- | --- | --- | --- | --- |
| 1 | 100 | 5.74 | 3.32 | 35.59 |
| 2 | 70 | 0.991 | 0.732 | 55.18 |
| 3 | 40 | 0.199 | 0.0407 | 4.89 |
| 4 | 80 | 1.41 | 0.549 | 12.54 |
| 5 | 40 | 0.446 | 0.329 | 50.69 |
| 6 | 50 | 0.174 | 0.954 | 10.03 |
| 7 | 100 | 39.08 | 35.99 | 51.03 |
| 8 | 70 | 0.265 | 1.36 | 2.48 |
| 9 | 90 | 2.18 | 2.22 | 6.02 |
| 10 | 90 | 4.09 | 4.24 | 19.13 |
| 11 | 40 | 0.589 | 0.0659 | 16.14 |
| 12 | 50 | 0.258 | 4.95 | 6.81 |
| 13 | 100 | 25.99 | 45.44 | 53.17 |
| 14 | 80 | 1.41 | 0.549 | 12.54 |

Animal antitumor activity testing can be conducted by various cancer xenograft models.

A compound of formula I can be administered alone or in combination with one or more other therapeutic agents, including but not limited 17a-Ethinylestradiol, Diethylstilbestrol, Testosterone, Prednisone, Fluoxymesterone, Dromostanolone propionate, Testolactone, Megestrolacetate, Methylprednisolone, Methyl-testosterone, Prednisolone, Triamcinolone, chlorotrianisene, Hydroxyprogesterone, Aminoglutethimide, Estramustine, Medroxypro-gesteroneacetate, Leuprolide, Flutamide, Toremifene, Zoladex, matrix metalloproteinase inhibitors, Suitable EGFR inhibitors include gefitinib, erlotinib, and cetuximab. Pan Her inhibitors include canertinib, EKB-569, and GW-572016. VEGF inhibitors, such as Avastin, ZD6474 and SU6668, vatalanib, BAY-43-9006, SU11248, CP-547632 and CEP-7055. Also included are Src inhibitors as well as Casodex@ (bicalutamide, Astra Zeneca), Tamoxifen, MEK-1 kinase inhibitors, MAPK kinase inhibitors, PI3 inhibitors, and PDGF inhibitors, such as imatinib. Also included are IGF1R inhibitors, inhibitors of non-receptor and receptor tyrosine kinases, and inhibitors of integrin signaling. Also included are anti-angiogenic and antivascular agents which, by interrupting blood flow to solid tumors, render cancer cells quiescent by depriving them of nutrition. Additional cytotoxic agents include, melphalan, hexamethyl melamine, thiotepa, cytarabin, idatrexate, trimetrexate, dacarbazine, L-asparaginase, camptothecin, topotecan, bicalutamide, flutamide, leuprolide, pyridobenzoindole derivatives, interferons, and interleukins. Additional anticancer agents include microtubule-stabilizing agents such as paclitaxel, docetaxel, 09/712, 352 filed on Nov. 14, 2000), C-4 methyl carbonate paclitaxel, epothilone A, epothilone B, epothilone C, epothilone D, desoxyepothilone A, desoxyepothilone and microtubule-disruptor agents. Also suitable are CDK inhibitors, an antiproliferative cell cycle inhibitor, epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors. Castration, which also renders androgen dependent carcinomas non-proliferative, may also be utilized. The possible combination therapy takes the form of fixed combinations or administration of a compound of the invention and one or more other therapeutic agents being staggered or given independently of one another, or the combined administration of fixed combinations and one or more other therapeutic agents.

A compound of formula I can besides or in addition be administered especially for tumor therapy in combination with chemotherapy, radiotherapy, surgical intervention, or a combination of these. Long term therapy is equally possible as is adjuvant therapy in the context of other treatment strategies, as described above. Other possible treatments are therapy to maintain the patient's status after tumor regression, or even chemopreventive therapy, for example in patients at risk. A compound of Formula I is useful in the treatment of a variety of cancers, including, but not limited to, the following: (a) carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma; (b) hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma; (c) hematopoietic tumors of myeloid lineage, including acute and chronic myelogenous leukemias, myelodysplastic syndrome and promyelocytic leukemia; (d) tumors of mesenchymal origin, including fibrosarcoma and rhabdomyosarcoma; (e) tumors of the central and peripheral nervous system, including astrocytoma, neuroblastoma, glioma and schwannomas; and (f) other tumors, including melanoma, seminoma, teratocarcinoma, osteosarcoma, xenoderoma pigmentosum, keratoctanthoma, thyroid follicular cancer and Kaposi's sarcoma.

A compound according to the invention is not only for management of humans, but also for the treatment of other warm-blooded animals, for example of commercially useful animals. Such a compound may also be used as a reference standard in the test systems described above to permit a comparison with other compounds.

Salts are especially the pharmaceutically acceptable salts of compounds of formula I. Suitable pharmaceutically acceptable salts will be apparent to those skilled in the art and include those described in J. Pharm. Sci., 1977, 66, 1-19, such as acid addition salts formed with inorganic acid e.g. hydrochloric, hydrobromic, sulphuric, nitric or phosphoric acid; and organic acids e.g. succinic, maleic, acetic, fumaric, citic, tartaric, benzoic, p-toluenesulfonic, methanesulfonic or naphthalenesulfonic acid. Other salts may be used, for example in the isolation or purification of compounds of formula (I) and are included within the scope of this invention.

The compounds of this invention may be in crystalline or non-crystalline form, and, if crystalline, may optionally be hydrated or solvated. This invention includes within its scope stoichiometric hydrates as well as compounds containing variable amount of water.

The invention extents to all isomeric forms including stereoisomers and geometric isomers of the compounds of formula (I) including enantimers and mixtures thereof e.g. racemates. The different isomeric forms may be separated or resolved one from the other by conventional methods, or any given isomer may be obtained by conventional synthetic methods or by stereospecific or asymmetric syntheses.

Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered transdermally using methods know to those skilled in the art (see, for example: Chien; "transdermal Controlled Systemic Medications"; Marcel Dekker, Inc.; 1987. Lipp et al. WO 94/04157 3 Mar. 1994).

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

For all regimens of use disclosed herein for compounds of formula I, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily rectal dosage regimen will preferably be from 0.01 to 200 mg/Kg of total body weight. The daily vaginal dosage regimen will preferably be from 0.01 to 200 mg/Kg of total body weight. The daily topical dosage regimen will preferably be from 0.01 to 200 mg administered between one to four times daily. The transdermal concentration will preferably be that required to maintain a daily dose of from 0.01 to 200 mg/Kg. The daily inhalation dosage regimen will preferably be from 0.01 to 200 mg/Kg of total body weight.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lives. Assays used to predict bioavailability include transport across human intestinal cell monolayers, including Caco-2 cell monolayers. Toxicity to cultured hepatocycles may be used to predict compound toxicity. Serum protein binding may be predicted from albumin binding assays. Compound half-life is inversely proportional to the frequency of dosage of a compound. In vitro half-lifes of compounds may be predicted from assays of microsomal half-life.

Representative illustrations of the preparation of the present invention are given in Scheme I-Scheme II. Those having skill in the art will recognize that the starting materials may be varied and additional steps may be employed to produce compounds encompassed by the present invention.

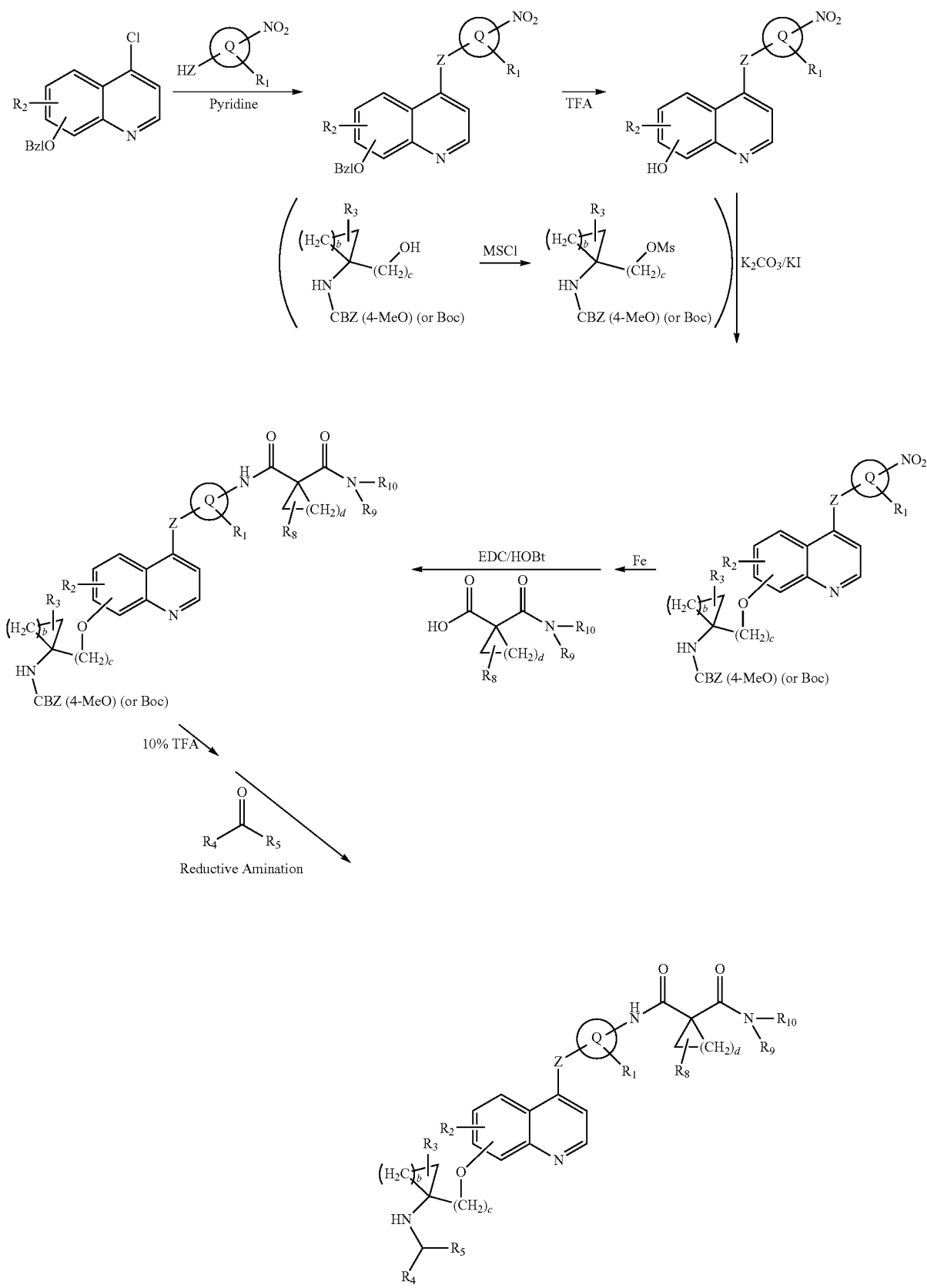

-continued
Scheme II
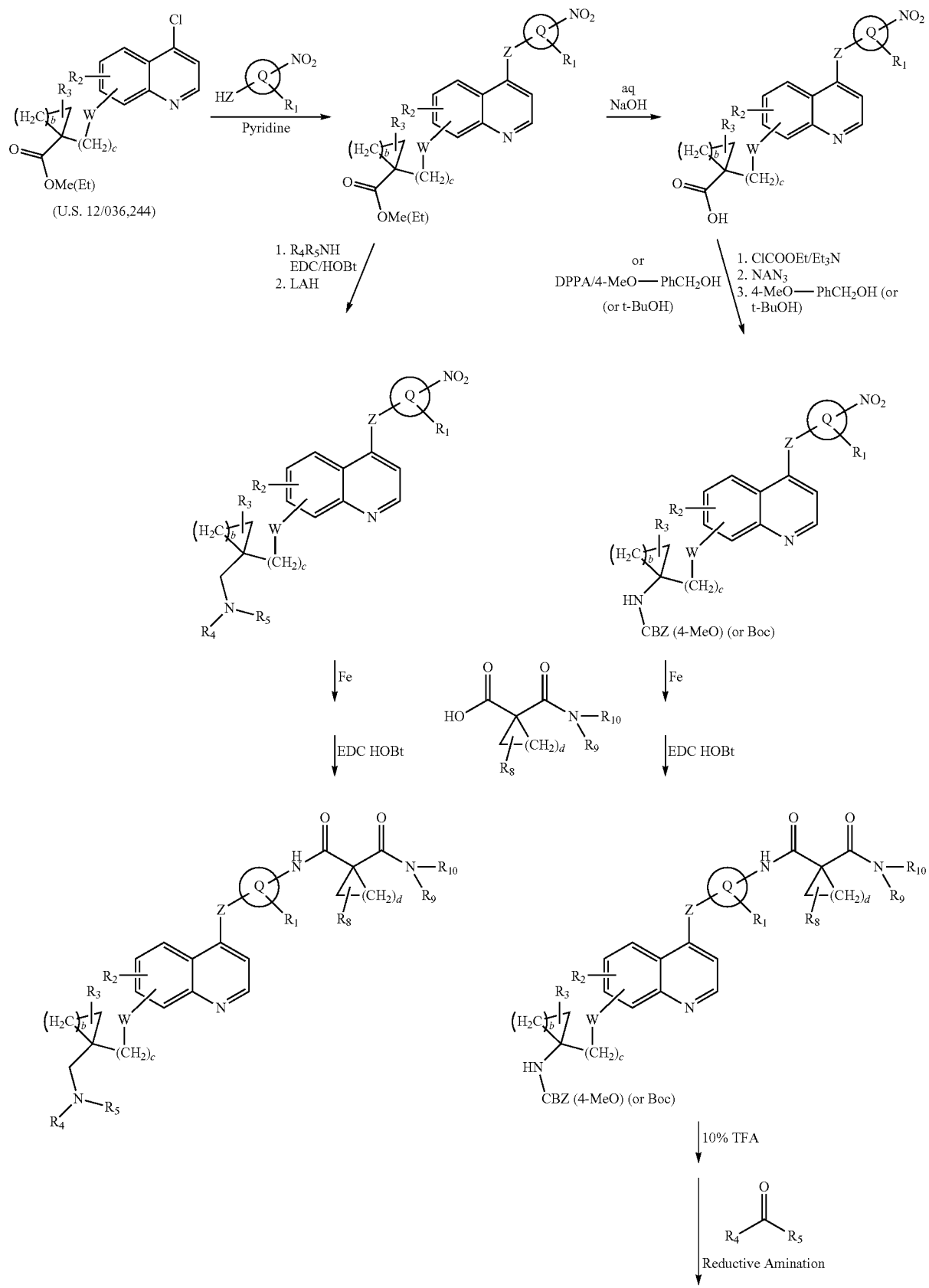

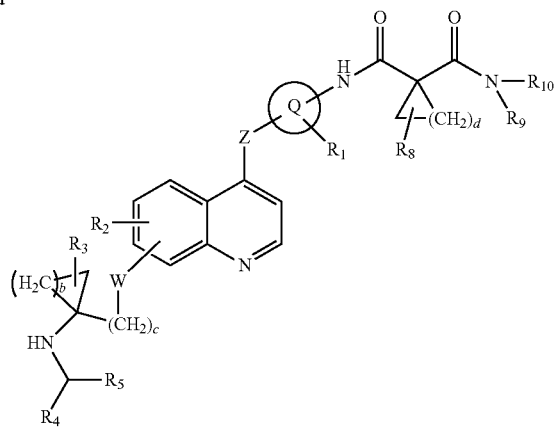

The following examples of Formula II, but not limited, can be prepared similarly according to the methods described in Scheme I-Scheme II.

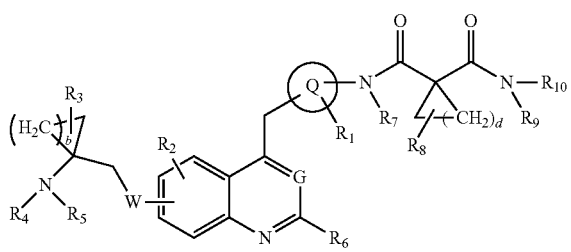

Formula II

Wherein

W and Z are each independently selected from O, or N—R;

G is selected from C—R, or N;

R is H;

$R_1$, $R_2$, $R_3$ and $R_8$ are each independently selected from H, halogen, halogeno-lower alkyl, lower alkyl, hydroxy, lower alkoxy;

$R_4$ and $R_5$ are each independently selected from H, halogen, halogeno-lower alkyl, lower alkyl, cycloalkyl, lower alkyl cycloalkyl, lower alkoxy, aryl, lower alkylaryl, heterocyclyl, lower alkylheterocyclyl, t-butyl-OC(=O)—, benzyl-OC(=O)—, 4-methoxybenzyl-OC(=O)—;

$R_6$, $R_7$ and $R_9$ are H;

$R_{10}$ is selected from a phenyl, a substituted phenyl, or a heterocyclyl;

b and d are selected from 1, 2 or 3;

ring Q is selected from a phenyl, a substituted phenyl or a pyridine;

or a pharmaceutically acceptable salt thereof.

The following examples of Formula III, but not limited, can also be prepared similarly according to the methods described in Scheme I-Scheme II.

Formula III

Wherein

W is selected from O, or N—R;

G is selected from C—R, or N;

R is H;

$R_1$ and $R_2$ are each independently selected from H, halogen, halogeno-lower alkyl, lower alkyl, hydroxy, lower alkoxy;

$R_4$ and $R_5$ are each independently selected from H, lower alkyl, cycloalkyl, lower alkyl cycloalkyl, lower alkoxy, aryl, lower alkylaryl, heterocyclyl, lower alkylheterocyclyl, t-butyl-OC(=O)—, benzyl-OC(=O)—, 4-methoxybenzyl-OC(=O)—;

$R_{10}$ is selected from a phenyl, a substituted phenyl, or a heterocyclyl;

or a pharmaceutically acceptable salt thereof.

The following examples of Formula IV, but not limited, can also be prepared similarly according to the methods described in Scheme I-Scheme II.

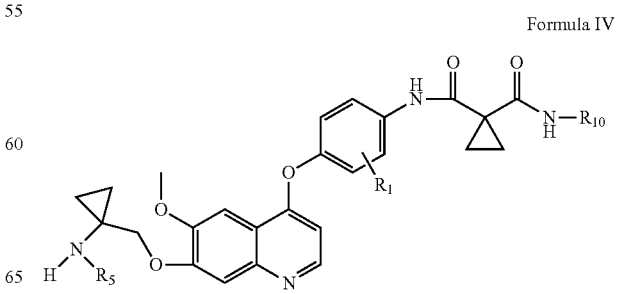

Formula IV

Wherein
R$_1$ is selected from 2-F or 3-F;
R$_5$ is selected from H, halogeno-lower alkyl, lower alkyl, cycloalkyl, lower alkyl cycloalkyl, aryl, lower alkylaryl, heterocyclyl, lower alkylheterocyclyl, t-butyl-OC(=O)—, benzyl-OC(=O)—, 4-methoxybenzyl-OC(=O)—;

R$_{10}$ is selected from a phenyl, a substituted phenyl, or a pyridine;

or a pharmaceutically acceptable salt thereof.

The following examples, but not limited, can also be prepared similarly according to the methods described in Scheme I-Scheme II.

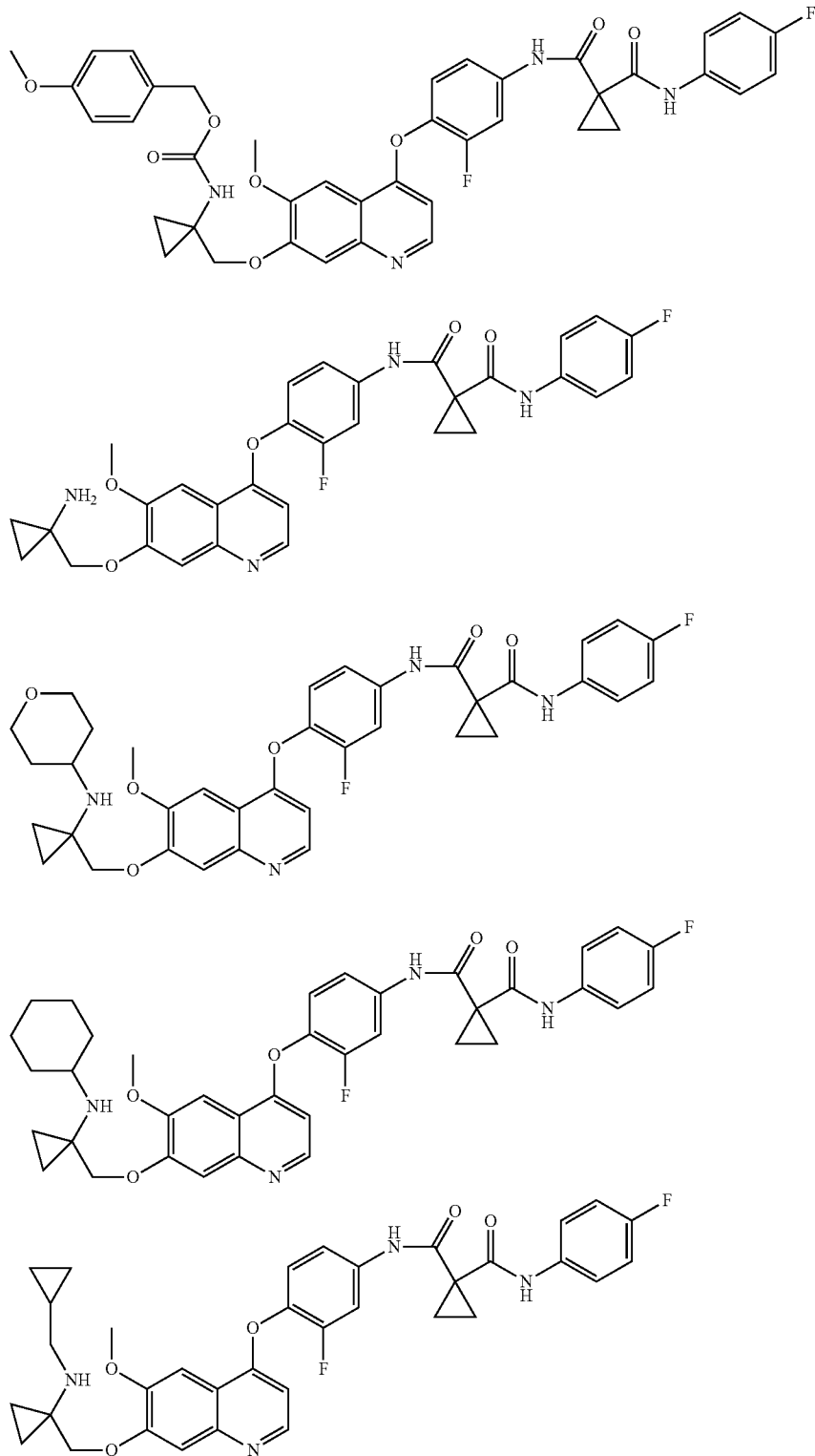

-continued
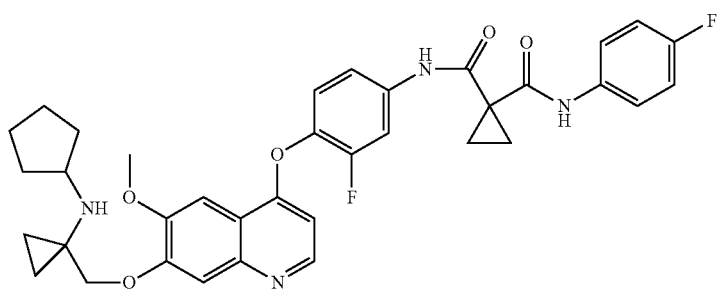
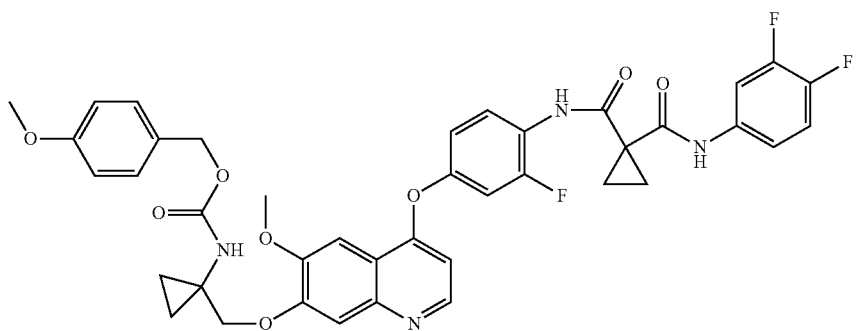
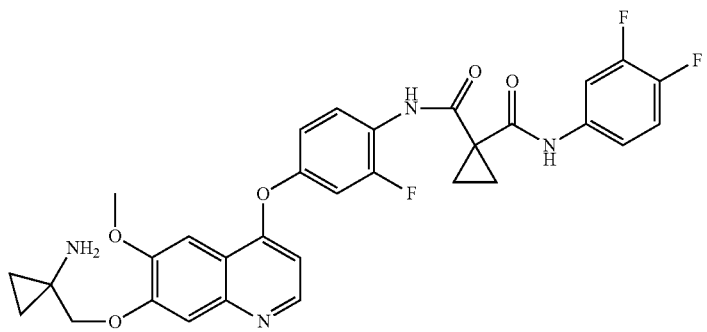
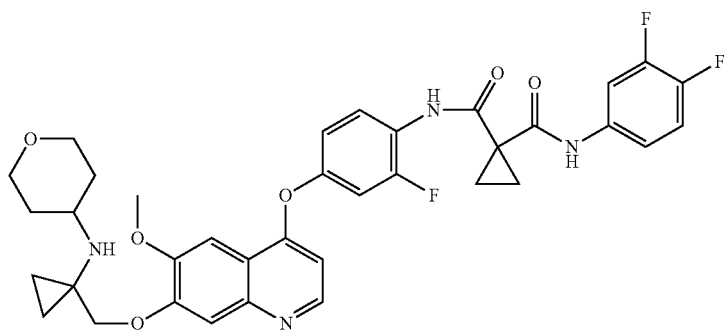
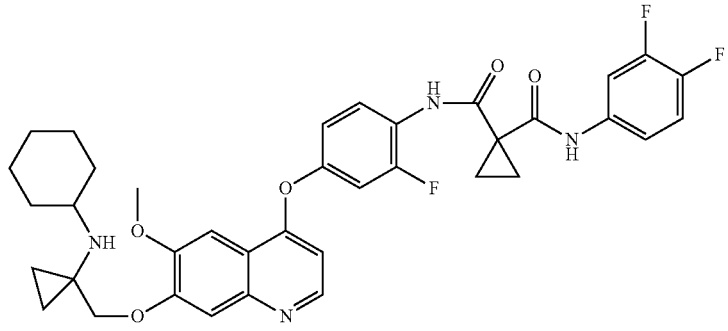

-continued
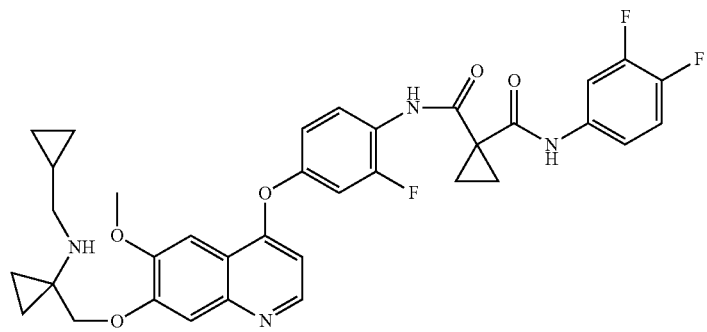
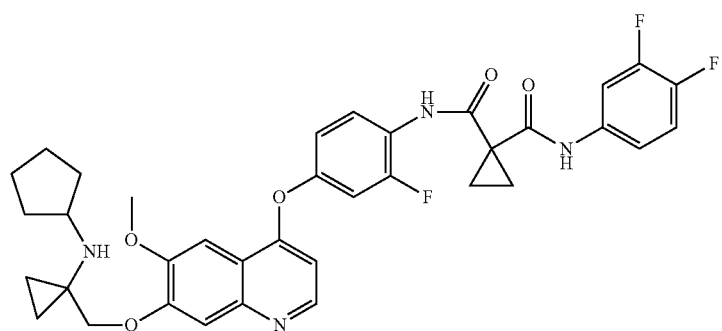
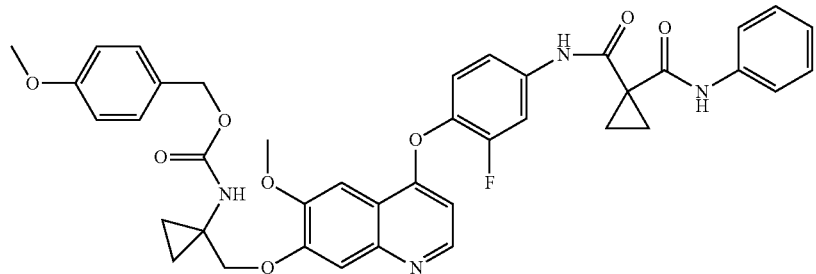
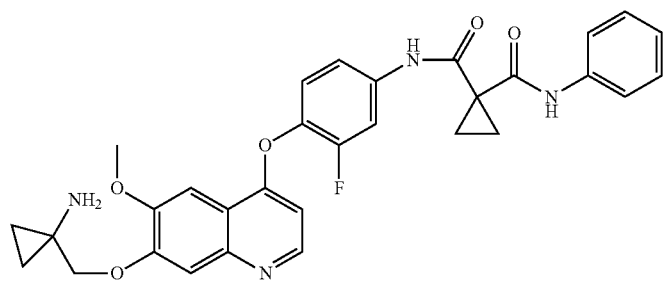
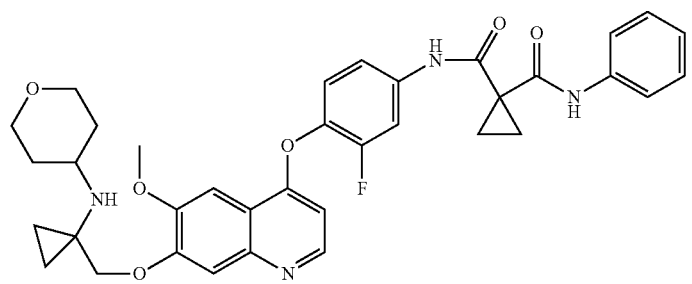

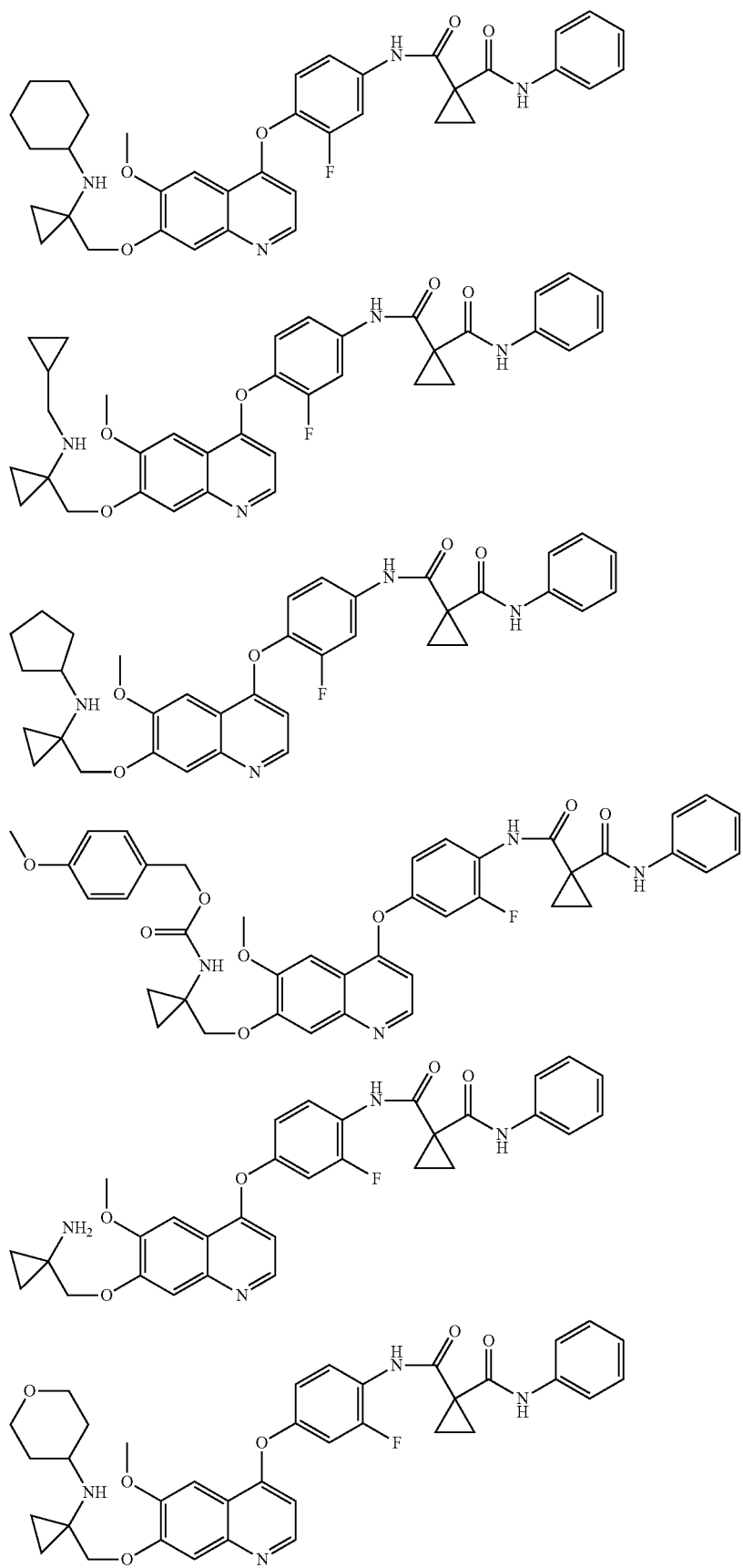

-continued
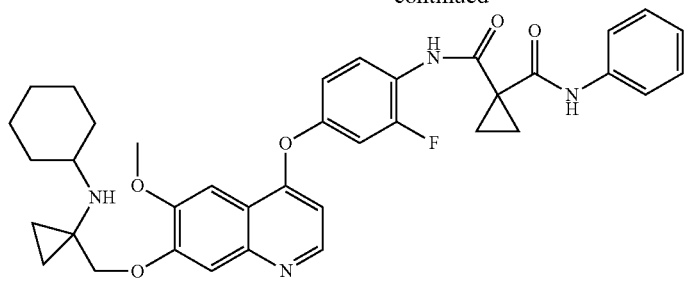
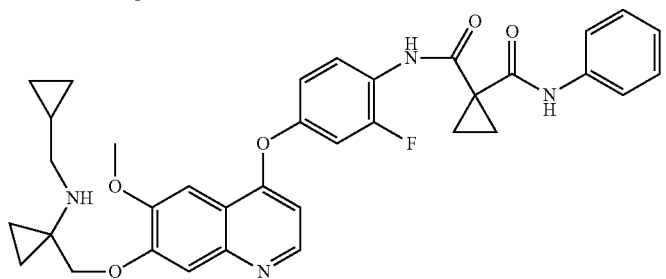
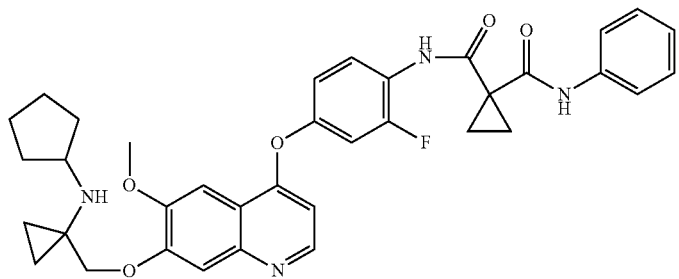
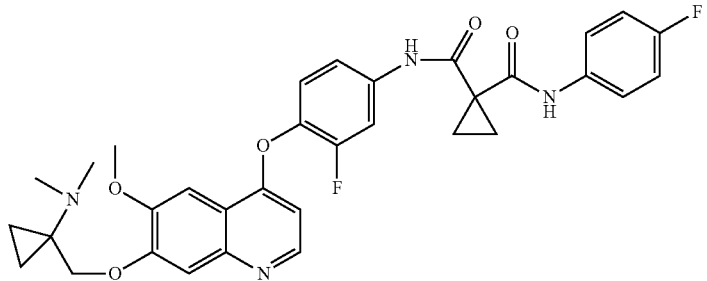
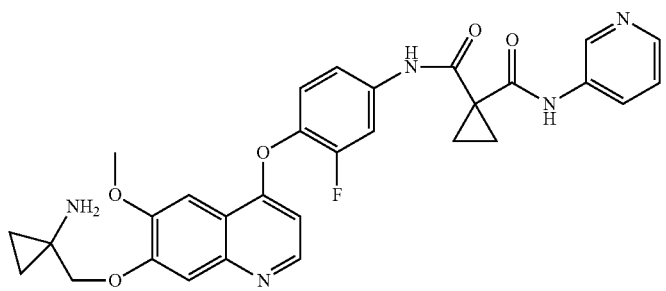
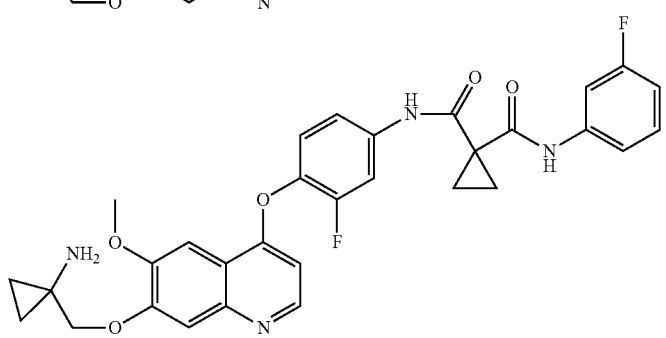

-continued
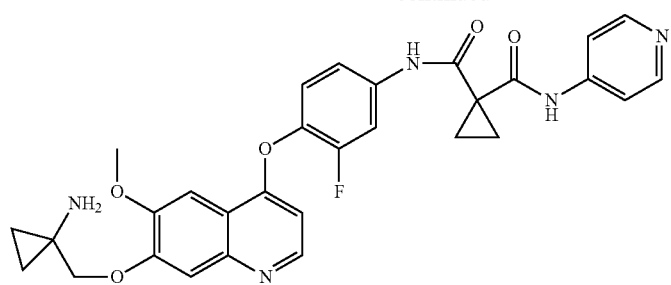
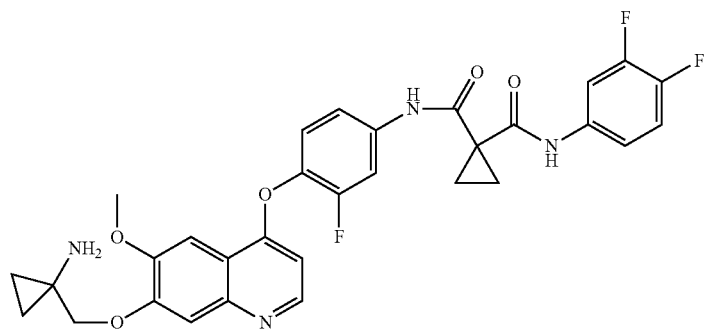
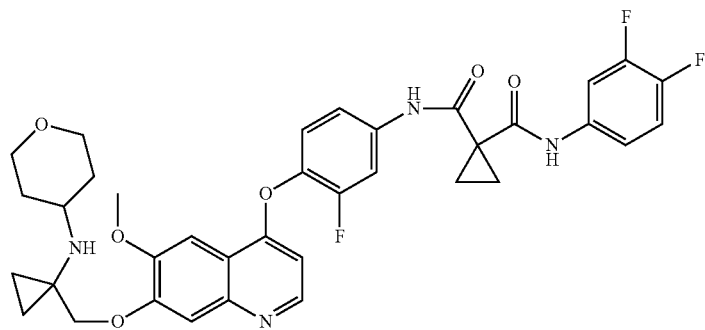
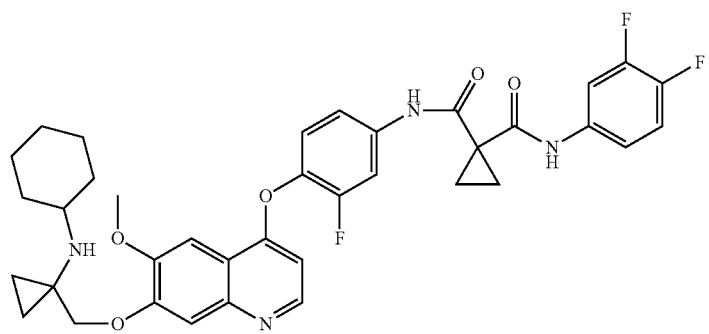
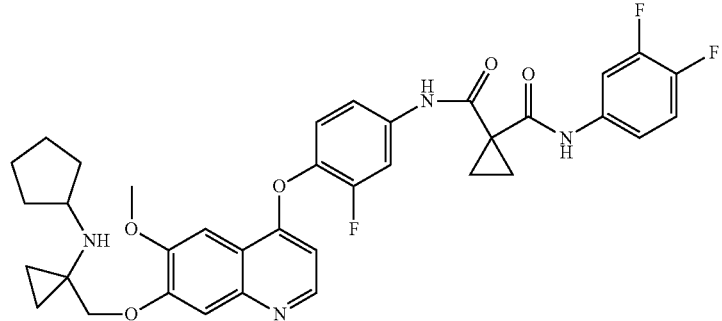

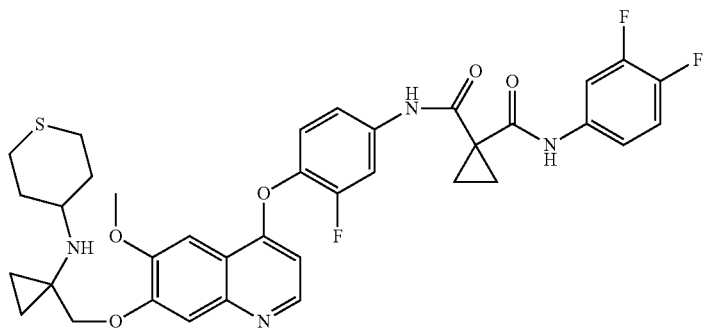
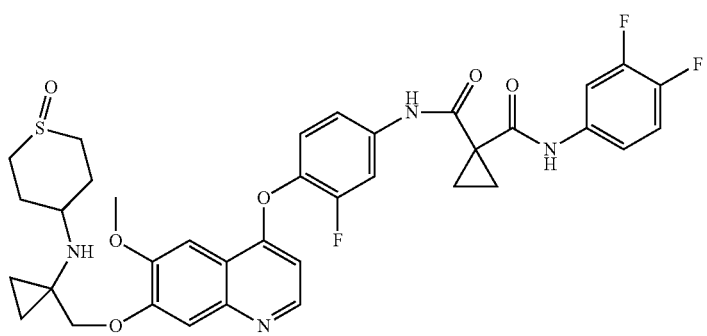
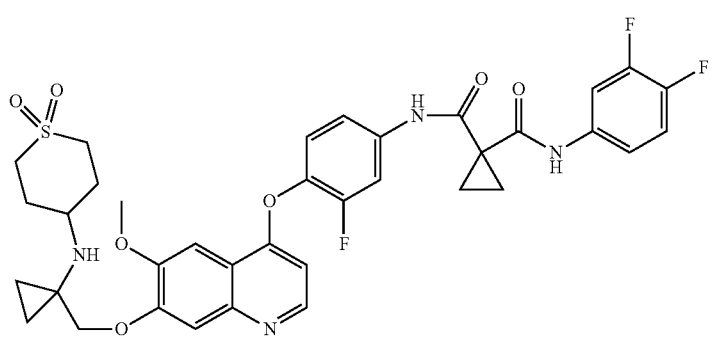
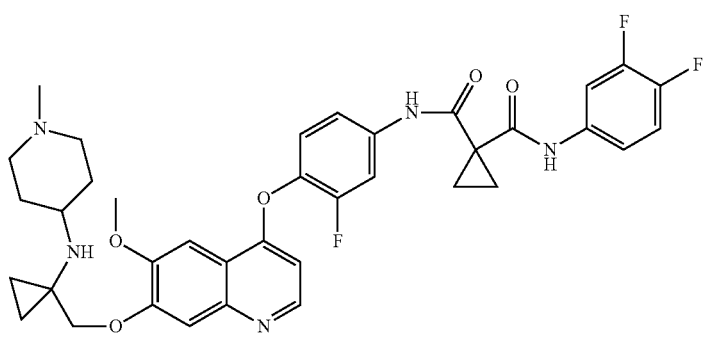
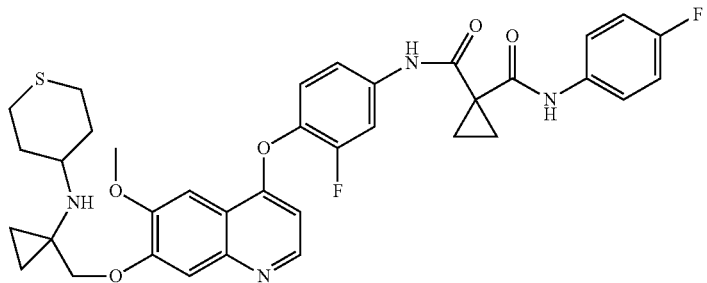

-continued
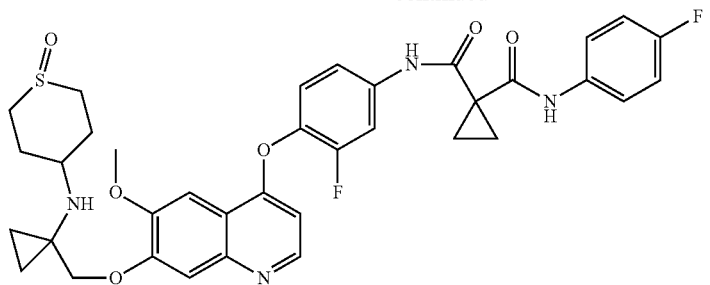
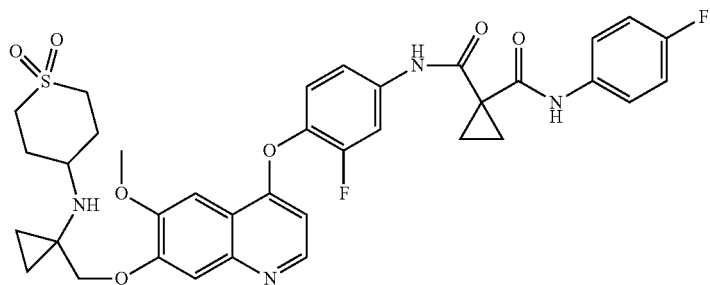
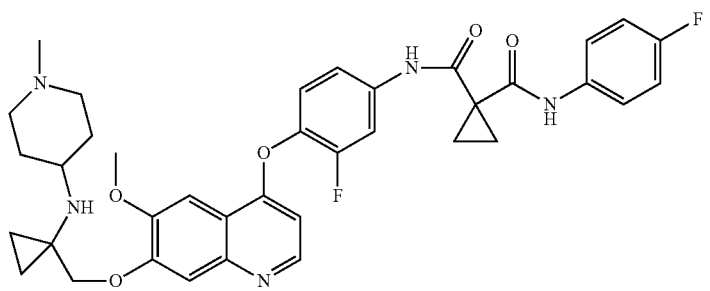
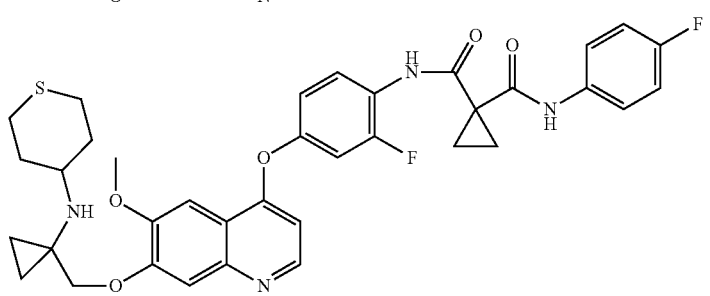
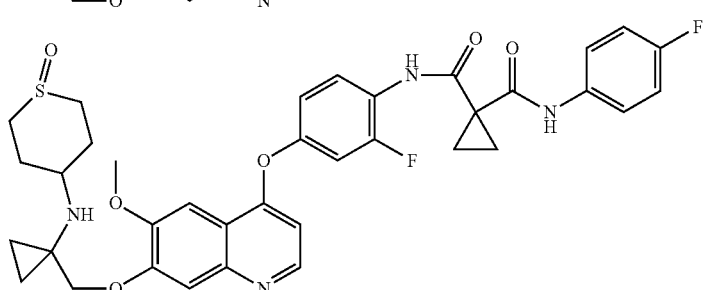
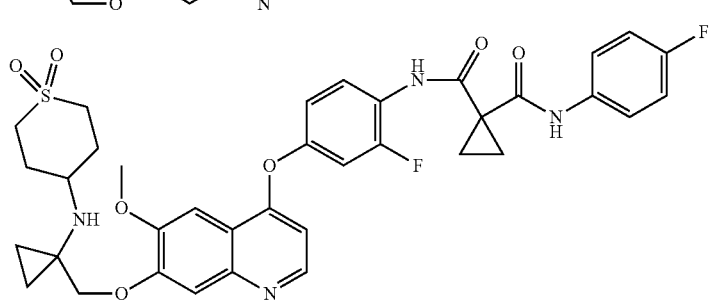

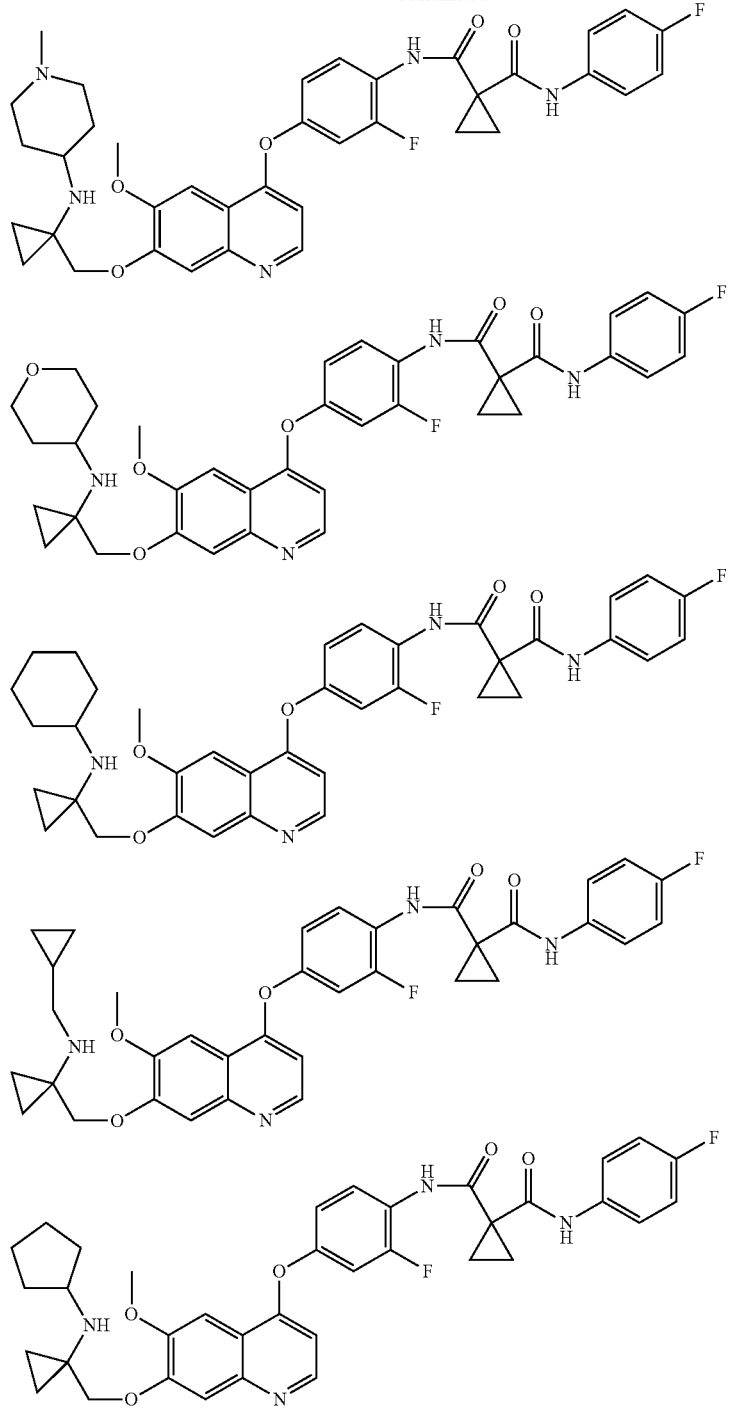

or a pharmaceutically acceptable salt thereof.

In some cases protection of certain reactive functionalities may be necessary to achieve some of above transformations. In general the need for such protecting groups will be apparent to those skilled in the art of organic synthesis as well as the conditions necessary to attach and remove such groups. Those skilled in the art will recognize that in certain instances it will be necessary to utilize different solvents or reagents to achieve some of the above transformations.

The disclosures in this application of all articles and references, including patents, are incorporated herein by reference in their entirety.

The invention is illustrated further by the following examples, which are not to be construed as limiting the invention in scope or spirit to the specific procedures described in them.

The starting materials are and various intermediates may be obtained from commercial sources, prepared from commercially available organic compounds, or prepared using well known synthetic methods.

Representative methods for preparing intermediates of the invention are set forth below in the examples.

The following abbreviations have been used and others are all standard chemical formula representation.

EtOH: ethanol, MeOH: methanol, RT: room temperature, DIPEA: diisopropylethylamine, DCM: Dichloromethane, DMF: N,N-dimethylformamide, EtOAc: ethyl acetate, HOBt: 1-hydroxybenzo-triazole hydrate, EDC: 1-(3-dimethylaminopropyl)-3-ethylcarbodiimide hydrochloride, MsCl: Methanesulfonyl chloride, eq: equivalent, g: gram, mg: milligram, ml: milliliter,

EXAMPLE 1

4-methoxybenzyl-1-((4-(2-fluoro-4-(1-(4-fluorophenylcarbamoyl)cyclopropanecarboxamido)-phenoxy)-6-methoxyquinolin-7-yloxy)methyl)cyclopropylcarbamate A mixture of Methyl 1-((4-chloro-6-methoxyquinolin-7-yloxy)methyl)cyclopropane-carboxylate (29.2 g, US12036244) and 2-fluoro-4-nitrophenol (20.5 mg) in pyridine (50 ml) was heated at 110° C. for 4 hours and cooled. The reaction was evaporated and water (300 ml) was added and further sonicated for 20 minutes. The solid was filtered and washed with water followed by acetone to give the product as methyl 1-((4-(2-fluoro-4-nitrophenoxy)-6-methoxyquinolin-7-yloxy)methyl)cyclopropanecarboxylate (32 g). This product (3.9 g) was mixed with LiOH (0.82 g) in THF/$H_2O$ (40 ml/20 ml) and the mixture was refluxed for 4 hours. The solution was evaporated and acidified with AcOH, the precipitated was filtered and washed with water followed by acetone to give the product as 1-((4-(2-fluoro-4-nitrophenoxy)-6-methoxyquinolin-7-yloxy)methyl)cyclo-propanecarboxylic acid. This acid (1 g) was mixed with DIPEA (0.53 ml) in acetone (50 ml) and cooled at 0° C. To the reaction mixture was added isobutylchloroformate slowly and further stirred for 1 hour at 0° C. To the reaction was added $NaN_3$ (1.52 g) in water (2 ml) and further stirred for 2 hours at 0° C. EtOAc (100 ml) was added to the reaction and washed with brine, dried over $Na_2SO_4$. The solution was evaporated to around 10 ml and toluene (70 ml) was added followed by addition of 4-methoxybenzyl alcohol. The solution was refluxed for 4 hours and cooled, EtOAc (50 ml) and water (50 ml) were added and further extracted with EtOAc two times. The combined organic layer was washed with water, brine and dried over $Na_2SO_4$. The solution was evaporated and purified with silica gel column to give 4-methoxybenzyl 1-((4-(2-fluoro-4-nitrophenoxy)-6-methoxyquinolin-7-yloxy)-methyl)cyclopropyl-carbamate (850 mg) that was mixed with Fe power (1 g) and $NH_4Cl$ (100 mg) in EtOH/$H_2O$ (20 ml, 16 ml/4 ml). The solution was refluxed for two hours and filtered through the Celite and washed with MeOH. The filtrate was evaporated and partitioned with water and DCM, the aqueous layer was further extracted with DCM twice. The combined organic layer was washed with water, brine and dried over $Na_2SO_4$. The solution was evaporated to give 4-methoxybenzyl 1-((4-(2-fluoro-4-aminophenoxy)-6-methoxyquinolin-7-yloxy)methyl)cyclopropylcarbamate (650 mg) for next step without further purification.

To a mixture of 1-(methoxycarbonyl)cyclopropanecarboxylic acid (4.2 g) and 4-fluoroaniline (3.3 g) in DCM (40 ml) was added EDC (7.4 g) and HOBt (4 g), the reaction was stirred at RT for 4 hours and washed with 1N HCl, $NaHCO_3$ solution, water, brine and dried over $Na_2SO_4$. The solution was evaporated and the residue was mixed with NaOH (3.2 g) and MeOH/H2O (60 ml/6 ml). The mixture was refluxed for 30 minutes then was evaporated. The residue was acidified with 4N HCl and the precipitate was filtered. The filter cake was washed with water followed by cold EtOH to give the product as 1-(4-fluorophenylcarbamoyl)-cyclopropanecarboxylic acid 2.8 g. This product (1.8 g) was mixed with DCM (30 ml) and two drops of DMF. Oxalyl chloride (1.2 ml) was added into the solution and the reaction was refluxed for one hour. The solvent was removed followed by adding DCM (20 ml) and DIPEA (1.3 ml). To the above solution was added 4-methoxybenzyl 1-((4-(2-fluoro-4-aminophenoxy)-6-methoxyquinolin-7-yloxy)-methyl)cyclopropylcarbamate (1.5 g), the reaction was stirred at RT for 4 hours. Saturated $NaHCO_3$ (30 ml) and DCM (80 ml) were added into the reaction, the solution was further extracted with DCM twice. The combined organic layer was washed with water, brine and dried over $Na_2SO_4$. The solution was evaporated and purified with silica gel column to give the titled compound 2.1 gram. Mass: (M+1), 739

EXAMPLE 2

N-(4-(7-((1-aminocyclopropyl)methoxy)-6-methoxyquinolin-4-yloxy)-3-fluorophenyl)-N-(4-fluorophenyl)cyclopropane-1,1-dicarboxamide The product of Example 1 (2.1 g) was mixed with 10% TFA/DCM (50 ml) and stirred at 0° C. for 2 hours. Saturated $NaHCO_3$ (80 ml) was added to the solution at 0° C. and the solution was further extracted with EtOAc twice. The combined organic layer was washed with water, brine and dried over $Na_2SO_4$. The solution was evaporated to give the titled compound for next step without further purification. Mass: (M+1), 575

EXAMPLE 3

N-(3-fluoro-4-(6-methoxy-7-((1-(tetrahydro-2H-pyran-4-ylamino)cyclopropyl)methoxy)quinolin-4-yloxy)phenyl)-N-(4-fluorophenyl)cyclopropane-1,1-dicarboxamide The product of Example 2 (200 mg) was mixed with tetrahydro-4H-pyran-4-one (45 mg), $NaHB(OAc)_3$ (96 mg) and HOAc (42 mg) in DCM (5 ml). The reaction mixture was stirred at 30° C. overnight. Saturated $NaHCO_3$ (20 ml) was added to the reaction and the solution was further extracted with EtOAc twice. The combined organic layer was washed with water, brine and dried over $Na_2SO_4$. The solution was evaporated and purified by preparative TLC plate to give the titled compound. Mass: (M+1), 659

EXAMPLE 4

N-(4-(7-((1-(cyclohexylamino)cyclopropyl)methoxy)-6-methoxyquinolin-4-yloxy)-3-fluoro-phenyl)-N-(4-fluorophenyl)cyclopropane-1,1-dicarboxamide The title compound was prepared by similar manner to Example 3, by using cyclohexanone instead of tetrahydro-4H-pyran-4-one. Mass: (M+1), 657

EXAMPLE 5

N-(4-(7-((1-(cyclopropylmethylamino)cyclopropyl)methoxy)-6-methoxyquinolin-4-yloxy)-3-fluorophenyl)-N-(4-fluorophenyl)cyclopropane-1,1-dicarboxamide The title compound was prepared by similar manner to Example 3, by using cyclopropanecarbaldehyde instead of tetrahydro-4H-pyran-4-one. Mass: (M+1), 629

EXAMPLE 6

N-(4-(7-((1-(cyclopentylamino)cyclopropyl)methoxy)-6-methoxyquinolin-4-yloxy)-3-fluoro-phenyl)-N-(4-fluorophenyl)cyclopropane-1,1-dicarboxamide The title compound was prepared by similar manner to Example 3, by using cyclopentanone instead of tetrahydro-4H-pyran-4-one. Mass: (M+1), 643

EXAMPLE 7

4-methoxybenzyl 1-((4-(4-(1-(3,4-difluorophenylcarbamoyl)cyclopropanecarboxamido)-3-fluoro-phenoxy)-6-methoxyquinolin-7-yloxy)methyl)cyclopropylcarbamate The title compound was prepared by similar manner to Example 1, by using 1-(3,4-difluorophenylcarbamoyl)cyclopropanecarboxylic acid instead of 1-(4-fluorophenylcarbamoyl)-cyclopropanecarboxylic acid. 3-Fluoro-4-Nitrophenol was used instead of 2-Fluoro-4-Nitrophenol. Mass: (M+1), 757

EXAMPLE 8

N-(4-(7-((1-aminocyclopropyl)methoxy)-6-methoxyquinolin-4-yloxy)-2-fluorophenyl)-N-(3,4-difluorophenyl)cyclopropane-1,1-dicarboxamide The title compound was prepared by similar manner to Example 2, by using the product of Example 7 instead of the product of Example 1. Mass: (M+1), 593

EXAMPLE 9

N-(3,4-difluorophenyl)-N-(2-fluoro-4-(6-methoxy-7-((1-(tetrahydro-2H-pyran-4-ylamino)-cyclopropyl)methoxy)quinolin-4-yloxy)phenyl)cyclopropane-1,1-dicarboxamide The title compound was prepared by similar manner to Example 3, by using the product of Example 8 instead of the product of Example 2. Mass: (M+1), 677

EXAMPLE 10

N-(4-(7-((1-(cyclohexylamino)cyclopropyl)methoxy)-6-methoxyquinolin-4-yloxy)-2-fluoro-phenyl)-N-(3,4-difluorophenyl)cyclopropane-1,1-dicarboxamide The title compound was prepared by similar manner to Example 4, by using the product of Example 8 instead of the product of Example 2. Mass: (M+1), 675

EXAMPLE 11

N-(4-(7-((1-(cyclopropylmethylamino)cyclopropyl)methoxy)-6-methoxyquinolin-4-yloxy)-2-fluorophenyl)-N-(3,4-difluorophenyl)cyclopropane-1,1-dicarboxamide The title compound was prepared by similar manner to Example 5, by using the product of Example 8 instead of the product of Example 2. Mass: (M+1), 647

EXAMPLE 12

N-(4-(7-((1-(cyclopentylamino)cyclopropyl)methoxy)-6-methoxyquinolin-4-yloxy)-2-fluoro-phenyl)-N-(3,4-difluorophenyl)cyclopropane-1,1-dicarboxamide The title compound was prepared by similar manner to Example 6, by using the product of Example 8 instead of the product of Example 2. Mass: (M+1), 661

EXAMPLE 13

4-methoxybenzyl 1-((4-(4-(1-(phenylcarbamoyl)cyclopropanecarboxamido)-2-fluoro-phenoxy)-6-methoxyquinolin-7-yloxy)methyl)cyclopropylcarbamate The title compound was prepared by similar manner to Example 1, by using 1-(phenylcarbamoyl)cyclopropanecarboxylic acid instead of 1-(4-fluorophenylcarbamoyl)-cyclopropanecarboxylic acid. Mass: (M+1), 721

EXAMPLE 14

N-(4-(7-((1-aminocyclopropyl)methoxy)-6-methoxyquinolin-4-yloxy)-2-fluorophenyl)-N-(phenyl)cyclopropane-1,1-dicarboxamide The title compound was prepared by similar manner to Example 2, by using the product of Example 13 instead of the product of Example 1. Mass: (M+1), 557

EXAMPLE 15

N-(phenyl)-N-(2-fluoro-4-(6-methoxy-7-((1-(tetrahydro-2H-pyran-4-ylamino)cyclopropyl)-methoxy)quinolin-4-yloxy)phenyl)cyclopropane-1,1-dicarboxamide The title compound was prepared by similar manner to Example 3, by using the product of Example 14 instead of the product of Example 2. Mass: (M+1), 641

EXAMPLE 16

N-(4-(7-((1-(cyclohexylamino)cyclopropyl)methoxy)-6-methoxyquinolin-4-yloxy)-2-fluoro-phenyl)-N-(phenyl)cyclopropane-1,1-dicarboxamide The title compound was prepared by similar manner to Example 4, by using the product of Example 14 instead of the product of Example 2. Mass: (M+1), 639

EXAMPLE 17
N-(4-(7-((1-(cyclopropylmethylamino)cyclopropyl)methoxy)-6-methoxyquinolin-4-yloxy)-2-fluorophenyl)-N-(phenyl)cyclopropane-1,1-dicarboxamide The title compound was prepared by similar manner to Example 5, by using the product of Example 14 instead of the product of Example 2. Mass: (M+1), 611

EXAMPLE 18
N-(4-(7-((1-(cyclopentylamino)cyclopropyl)methoxy)-6-methoxyquinolin-4-yloxy)-2-fluoro-phenyl)-N-(phenyl)cyclopropane-1,1-dicarboxamide The title compound was prepared by similar manner to Example 6, by using the product of Example 14 instead of the product of Example 2. Mass: (M+1), 625

Examples of Salt Formation:

One compound from Example 1-18 (100 mg) was dissolved into EtOAc (1 ml) and to the solution was added 2N HCl/Ether solution (0.5 ml). The solution was evaporated to give a off white solid as its HCl salt.

One compound from Example 1-18 (100 mg) was mixed with EtOH (1 ml) and to the mixture was added tartaric acid (80 mg). The reaction was refluxed for 30 minutes and cooled at RT. The precipitate was filtered to give the tartaric acid salt.

The other pharmaceutical acceptable salts, such as hydrobromic, sulphuric, nitric, phosphoric acid; or succinic, maleic, acetic, fumaric, citric, benzoic, p-toluenesulfonic, methanesulfonic, naphthalenesulfonic acid salt can be prepared in the similar manner. It can be made at higher temperatures with EtOH, MeOH or isopropanol as well as with other pharmaceutical acceptable solvents.

EXAMPLES OF FORMULATION

The following are the examples of the formulations and these are purely illustrative and in no way to be interpreted as restrictive.

Formulation Example 1

Each capsule contains:

| | |
|---|---|
| One Compound from Example 1-18 | 100.0 mg |
| Corn starch | 23.0 mg |
| Calcium carboxymethyl cellulose | 22.5 mg |
| Hydroxypropylmethyl cellulose | 3.0 mg |
| Magnesium stearate | 1.5 mg |
| | 150.0 mg |

Formulation Example 2

A solution contains:

| | |
|---|---|
| One Compound from Example 1-18 | 1 to 10 g |
| Acetic acid or sodium hydroxide | 0.5 to 1 g |
| Ethyl p-hydroxybenzoate | 0.1 g |
| Purified water | 88.9 to 98.4 g |
| | 100.0 g |

Formulation Example 3

A powder for admixing with feedstuff contains:

| | |
|---|---|
| One Compound from Example 1-18 | 1 to 10 g |
| Corn starch | 98.5 to 89.5 g |
| Light anhydrous silicic acid | 0.5 g |
| | 100.0 g |

What is claimed is:

1. A compound represented by formula II

Formula II

Wherein
W and Z are each independently selected from O;
G is selected from C—R;
R is H;
$R_1$, $R_2$, $R_3$ and $R_8$ are each independently selected from H, halogen, halogeno-lower alkyl, lower alkyl, hydroxy, lower alkoxy;
$R_4$ and $R_5$ are each independently selected from H, halogen, halogeno-lower alkyl, lower alkyl, cycloalkyl, lower alkyl cycloalkyl, lower alkoxy, aryl, lower alkylaryl, heterocyclyl, lower alkylheterocyclyl, t-butyl-OC(=O)—, benzyl-OC(=O)—, 4-methoxybenzyl-OC(=O)—;
$R_6$, $R_7$ and $R_9$ are H;
$R_{10}$ is selected from a phenyl, a substituted phenyl, or a heterocyclyl;
b and d are selected from 1, 2 or 3;
ring Q is selected from a phenyl or a substituted pheny;
or a pharmaceutically acceptable salt thereof.

2. A compound according to claim 1, represented by formula III

Formula III

Wherein
W is selected from O;
G is selected from C—R;
R is H;
$R_1$ and $R_2$ are each independently selected from H, halogen, halogeno-lower alkyl, lower alkyl, hydroxy, lower alkoxy ;
$R_4$ and $R_5$ are each independently selected from H, lower alkyl, cycloalkyl, lower alkyl cycloalkyl, lower alkoxy, aryl, lower alkylaryl, heterocyclyl, lower alkylheterocyclyl, t-butyl-OC(=O)—, benzyl-OC(=O)—, 4-methoxybenzyl-OC(=O)—;
$R_{10}$ is selected from a phenyl, a substituted phenyl, or a heterocyclyl;
or a pharmaceutically acceptable salt thereof.

3. A compound according to claim 1, represented by formula IV

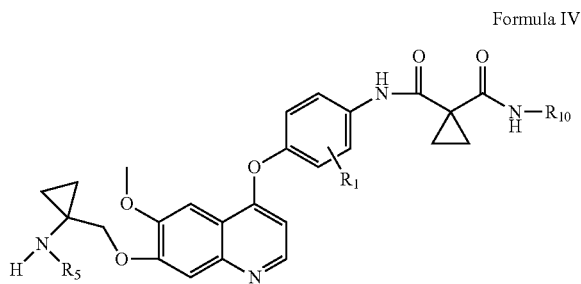

Formula IV

Wherein $R_1$ is selected from 2-F or 3-F;

$R_5$ is selected from H, halogeno-lower alkyl, lower alkyl, cycloalkyl, lower alkyl cycloalkyl, aryl, lower alkylaryl, heterocyclyl, lower alkylheterocyclyl, t-butyl-OC(=O)—, benzyl-OC(=O)—, 4-methoxybenzyl-OC(=O)—;

$R_{10}$ is selected from a phenyl, a substituted phenyl, or a pyridine;

or a pharmaceutically acceptable salt thereof.

4. A compound according to claim 1 that is selected from the group consisting of:

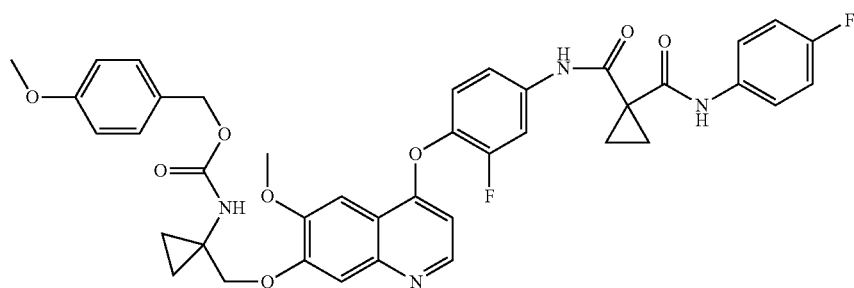

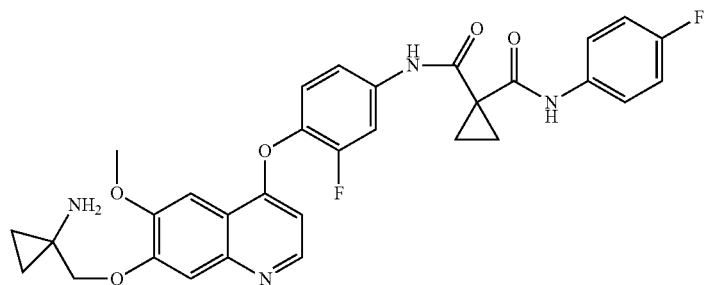

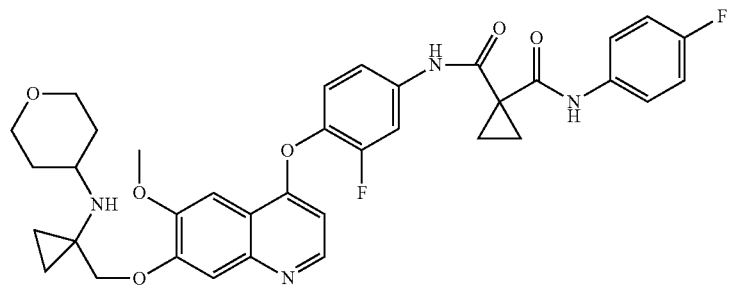

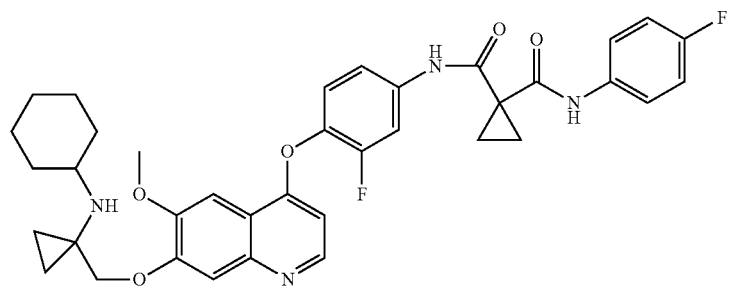

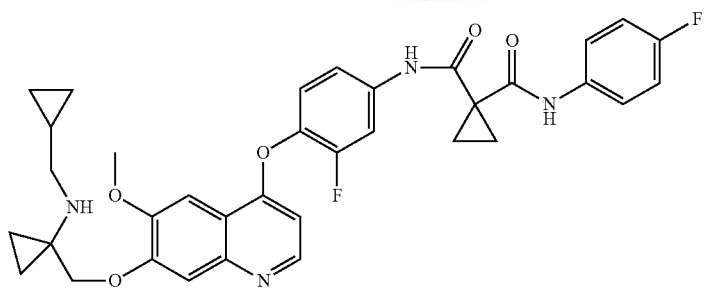
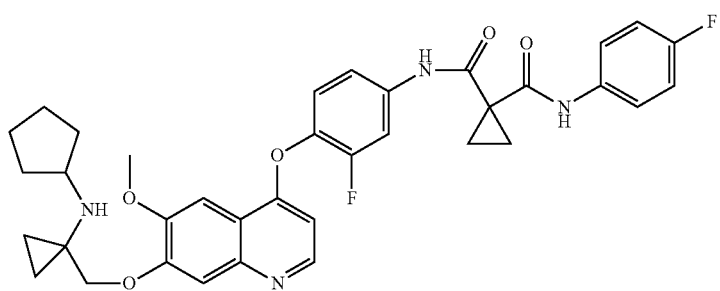
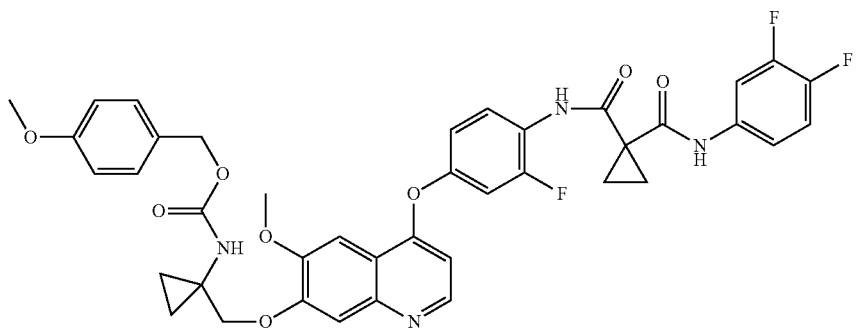
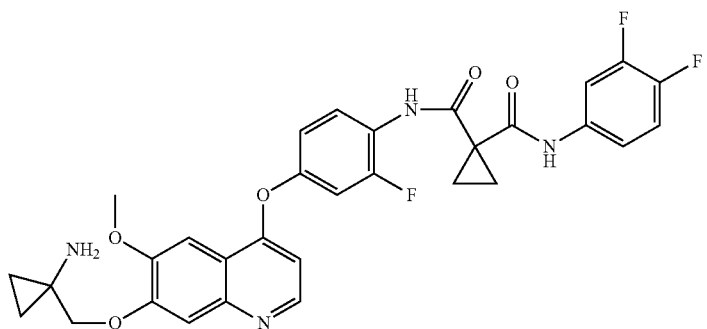
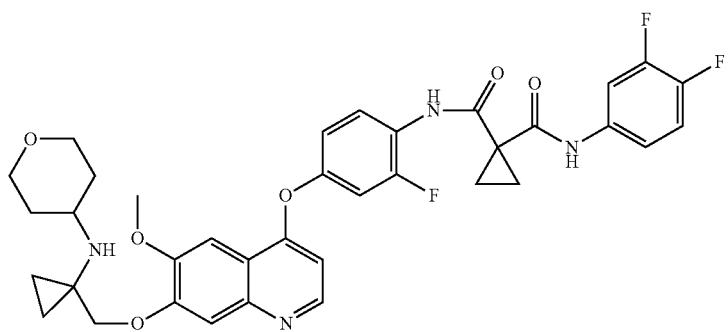

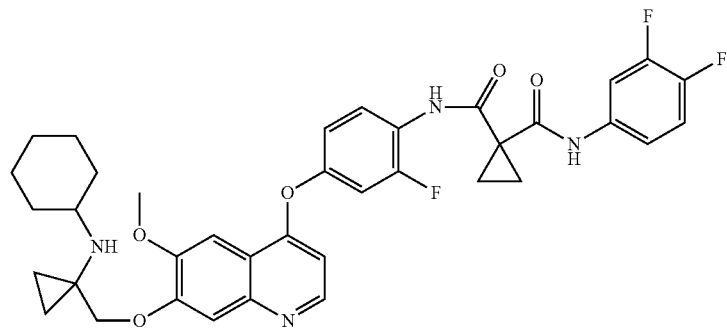
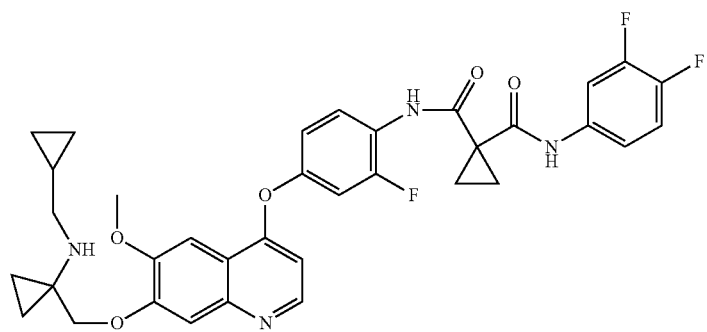
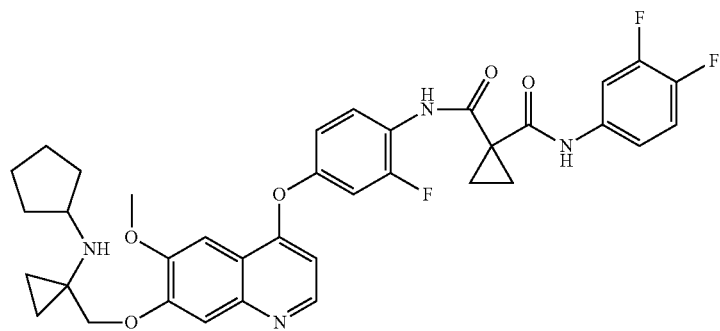
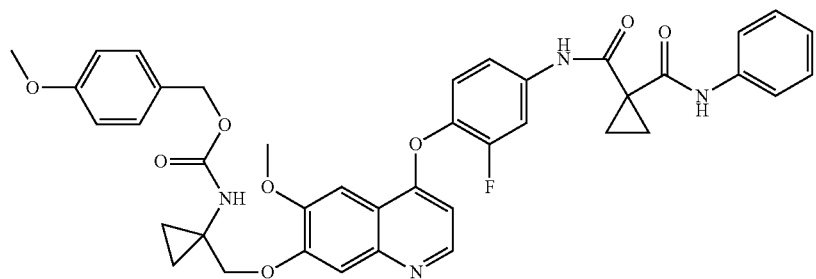
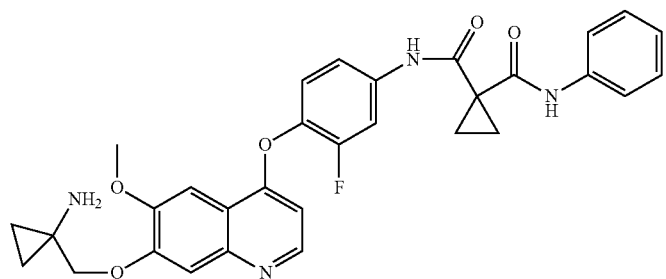

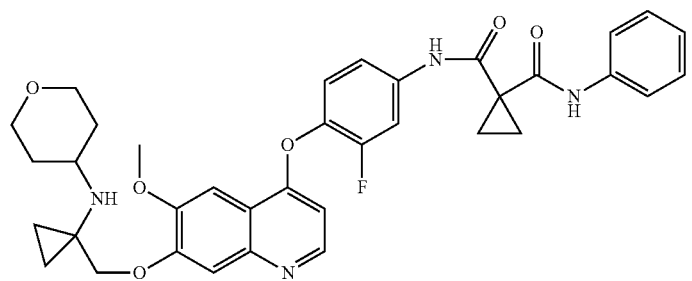
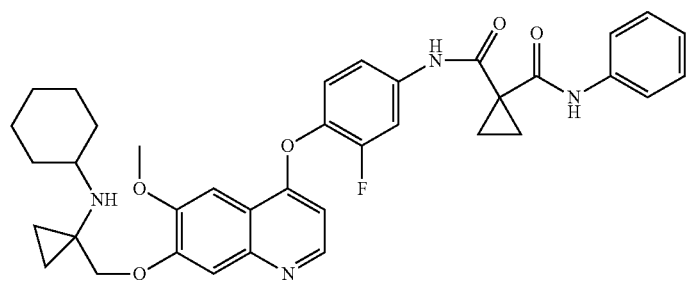
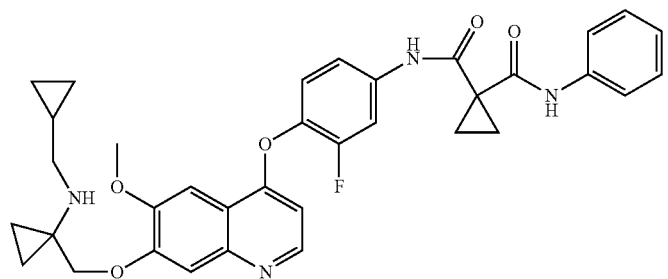
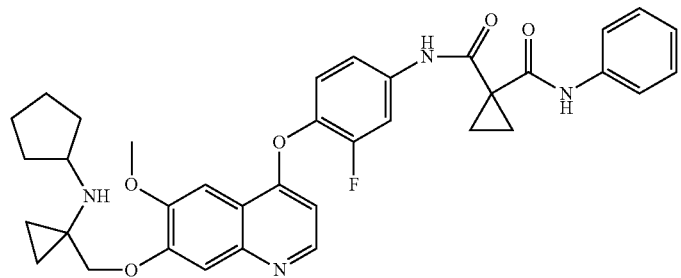
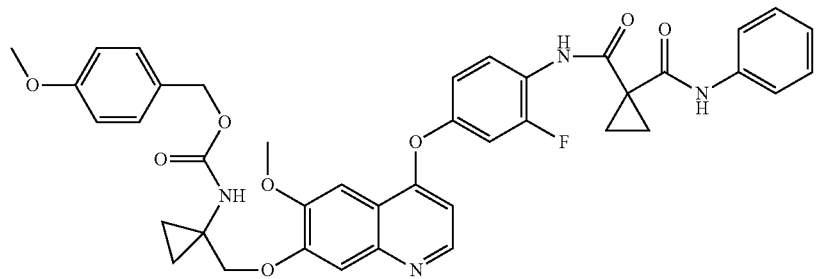
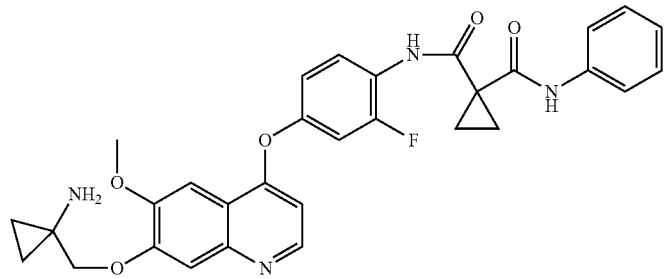

-continued
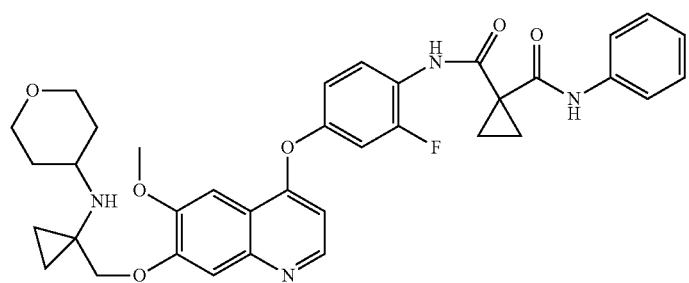
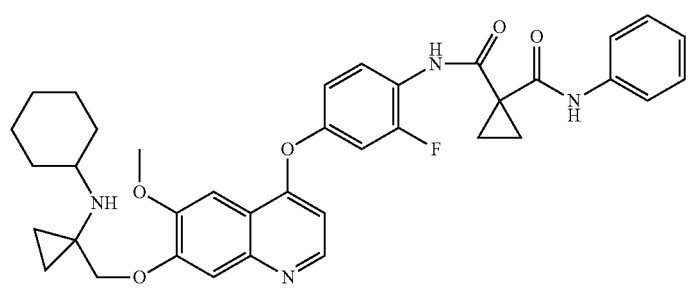
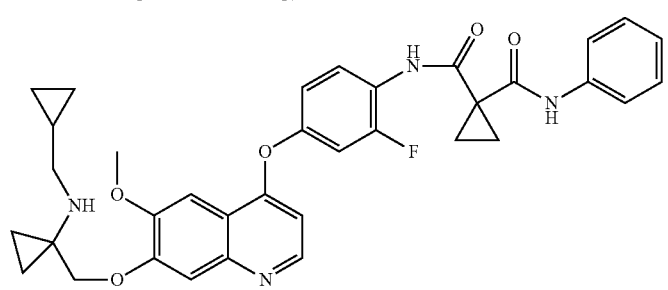
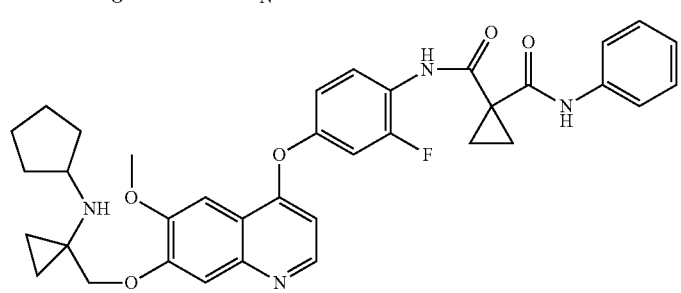
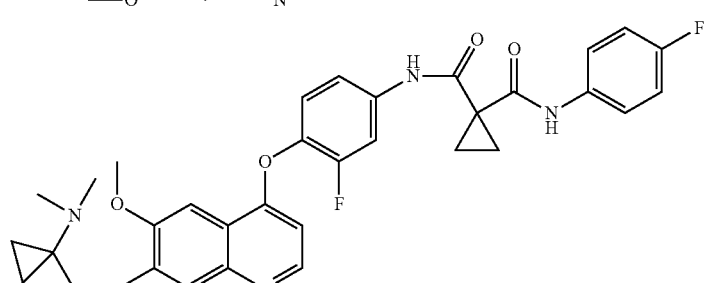
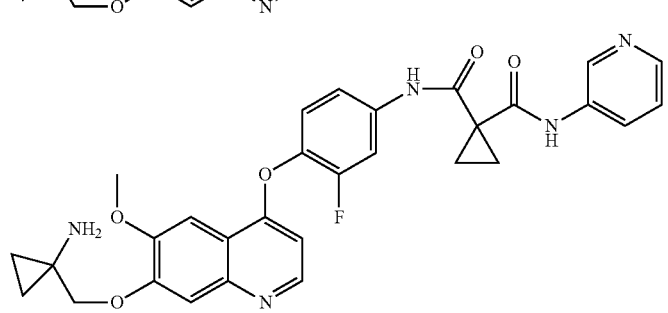

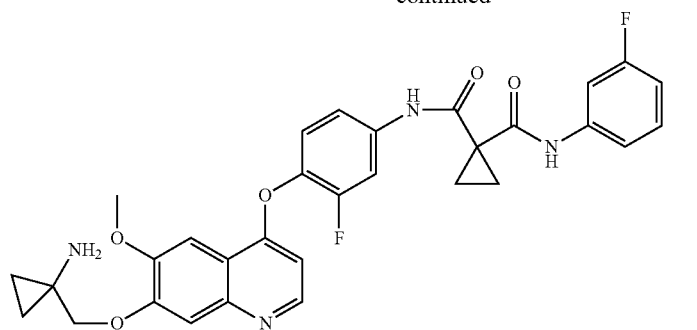
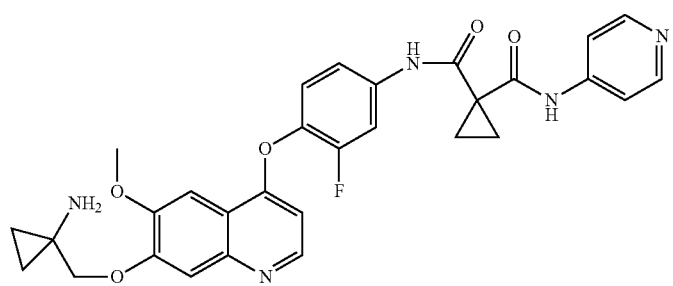
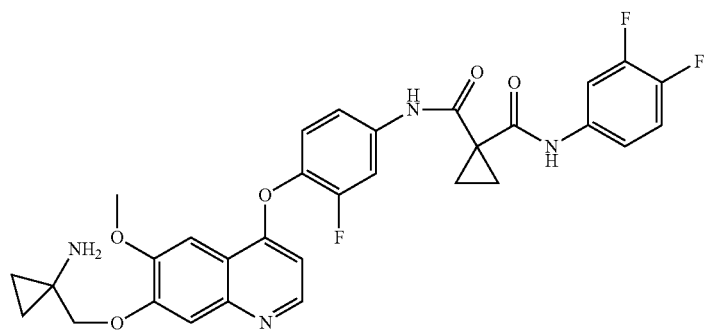
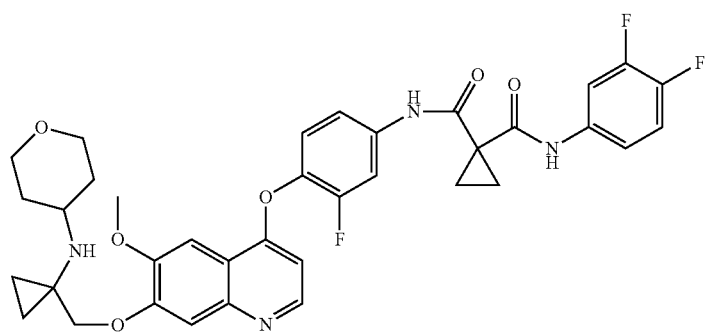
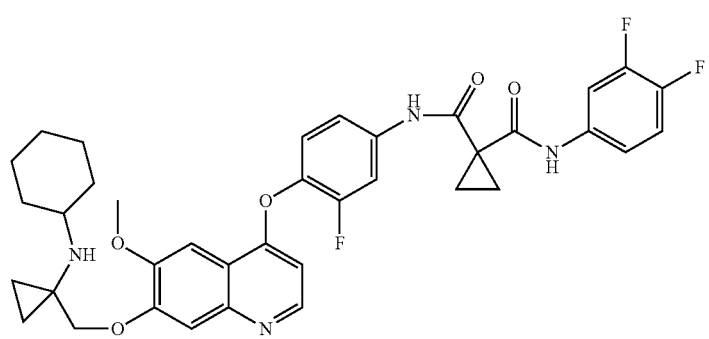

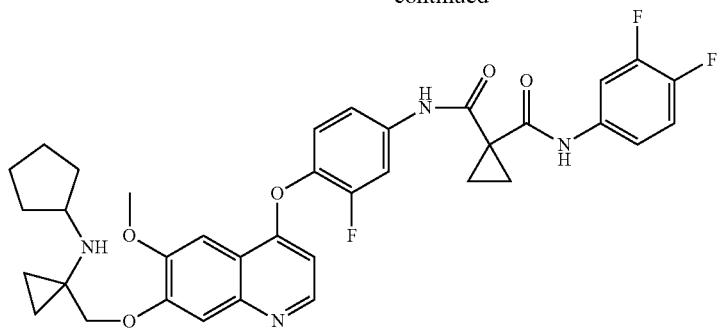
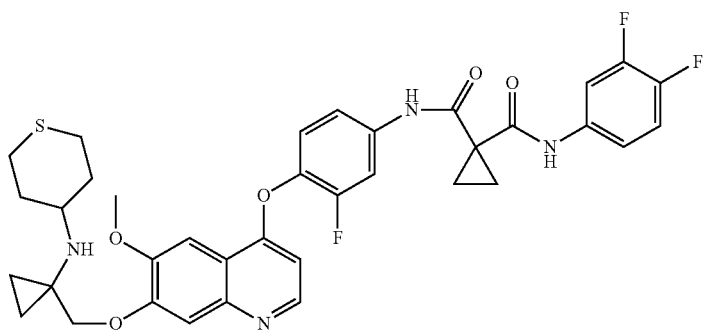
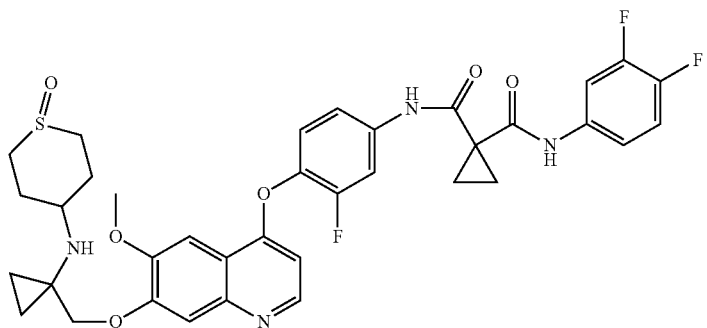
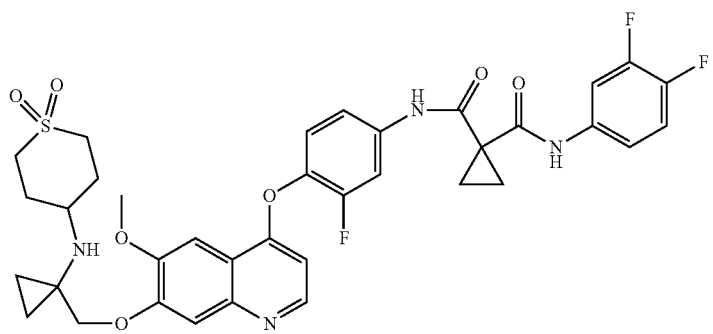
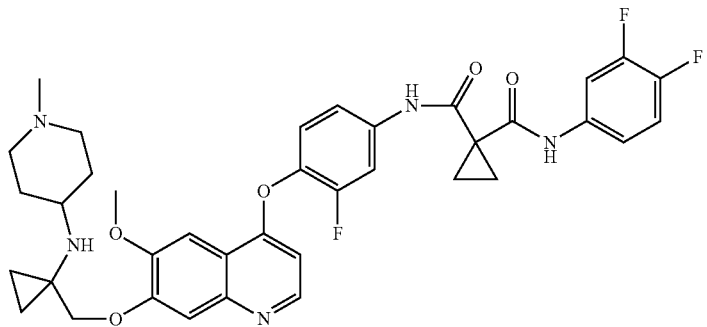

-continued
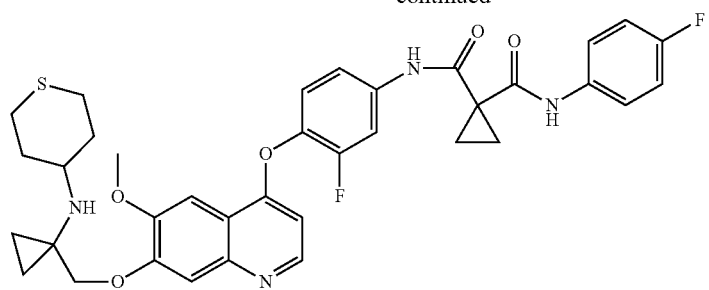
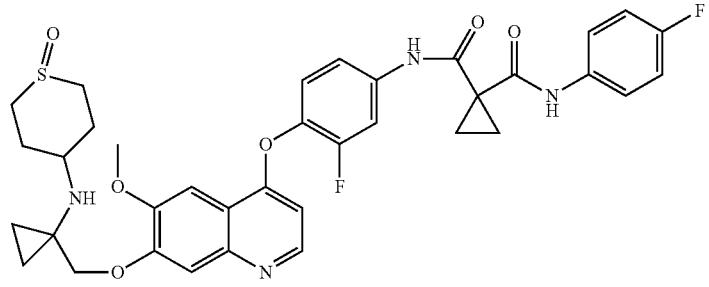
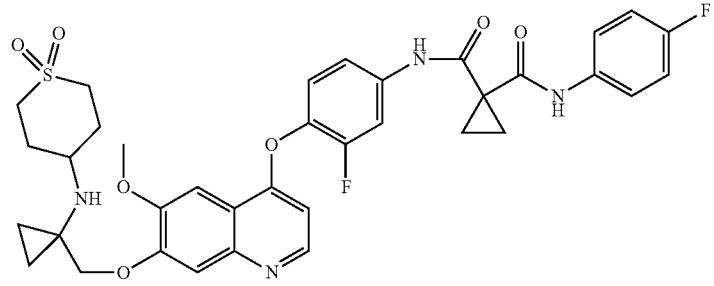
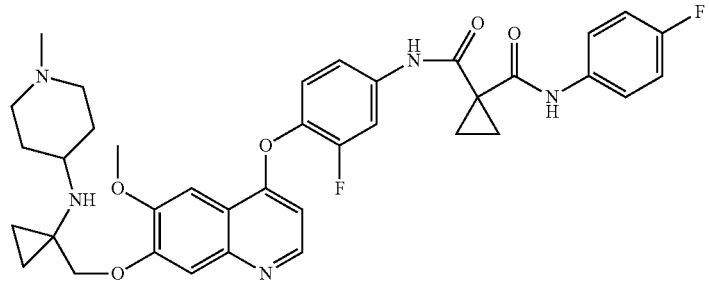
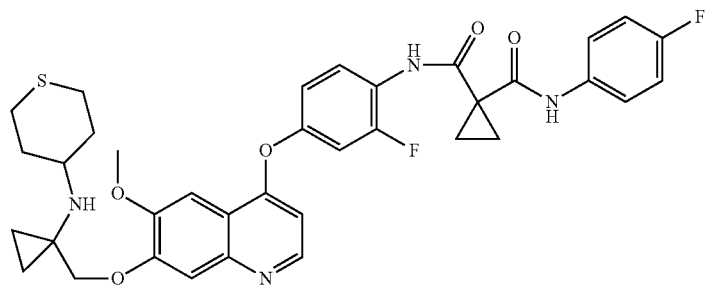
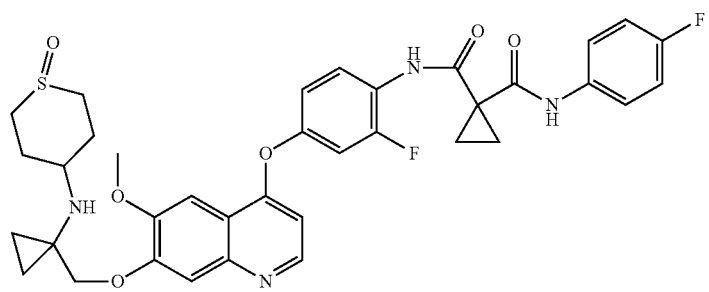

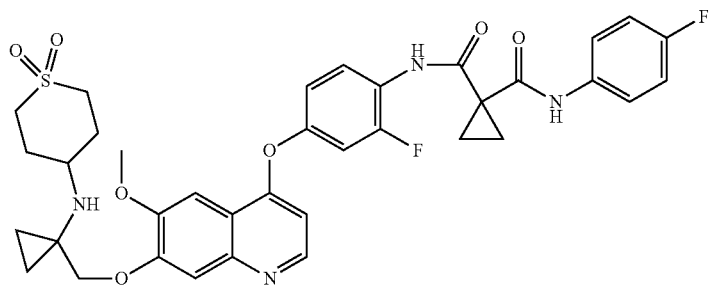
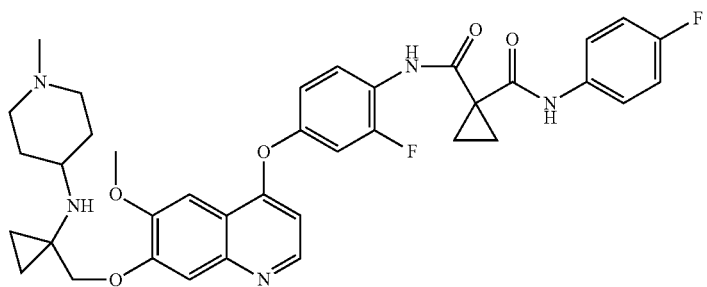
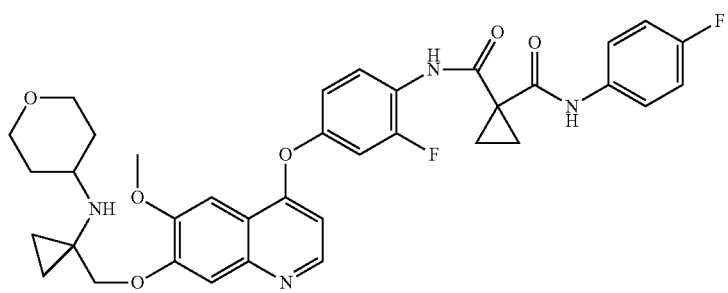
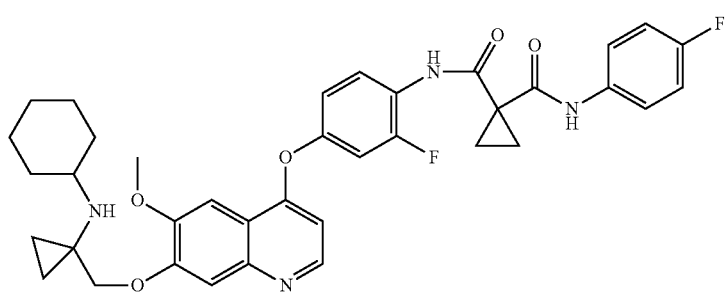
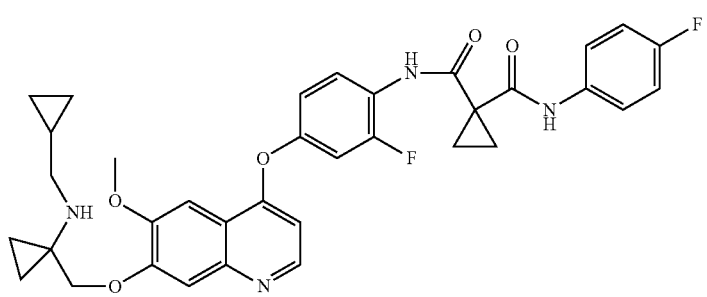

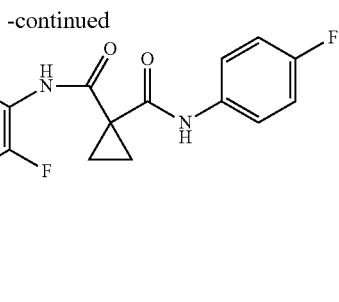

or a pharmaceutically acceptable salt thereof.

5. A compound according to claim 1 that is selected from the group consisting of:

- 4-methoxybenzyl-1-((4-(2-fluoro-4-(1-(4-fluorophenyl-carbamoyl)cyclopropanecarboxamido)-phenoxy)-6-methoxyquinolin-7-yloxy)methyl)cyclopropylcarbamate
- N-(4-(7-((1-aminocyclopropyl)methoxy)-6-methoxyquinolin-4-yloxy)-3-fluorophenyl)-N-(4-fluorophenyl)cyclopropane-1,1-dicarboxamide
- N-(3-fluoro-4-(6-methoxy-7-((1-(tetrahydro-2H-pyran-4-ylamino)cyclopropyl)methoxy)quinolin-4-yloxy)phenyl)-N-(4-fluorophenyl)cyclopropane-1,1-dicarboxamide
- N-(4-(7-((1-(cyclohexylamino)cyclopropyl)methoxy)-6-methoxyquinolin-4-yloxy)-3-fluoro-phenyl)-N-(4-fluorophenyl)cyclopropane-1,1-dicarboxamide
- N-(4-(7-((1-(cyclopropylmethylamino)cyclopropyl)methoxy)-6-methoxyquinolin-4-yloxy)-3-fluorophenyl)-N-(4-fluorophenyl)cyclopropane-1,1-dicarboxamide
- N-(4-(7-((1-(cyclopentylamino)cyclopropyl)methoxy)-6-methoxyquinolin-4-yloxy)-3-fluoro-phenyl)-N-(4-fluorophenyl)cyclopropane-1,1-dicarboxamide
- 4-methoxybenzyl 1-((4-(4-(1-(3,4-difluorophenylcarbamoyl)cyclopropanecarboxamido)-3-fluoro-phenoxy)-6-methoxyquinolin-7-yloxy)methyl)cyclopropylcarbamate
- N-(4-(7-((1-aminocyclopropyl)methoxy)-6-methoxyquinolin-4-yloxy)-2-fluorophenyl)-N-(3,4-difluorophenyl)cyclopropane-1,1-dicarboxamide
- N-(3,4-difluorophenyl)-N-(2-fluoro-4-(6-methoxy-7-((1-(tetrahydro-2H-pyran-4-ylamino)-cyclopropyl)methoxy)quinolin-4-yloxy)phenyl)cyclopropane-1,1-dicarboxamide
- N-(4-(7-((1-(cyclohexylamino)cyclopropyl)methoxy)-6-methoxyquinolin-4-yloxy)-2-fluoro-phenyl)-N-(3,4-difluorophenyl)cyclopropane-1,1-dicarboxamide
- N-(4-(7-((1-(cyclopropylmethylamino)cyclopropyl)methoxy)-6-methoxyquinolin-4-yloxy)-2-fluorophenyl)-N-(3,4-difluorophenyl)cyclopropane-1,1-dicarboxamide
- N-(4-(7-((1-(cyclopentylamino)cyclopropyl)methoxy)-6-methoxyquinolin-4-yloxy)-2-fluoro-phenyl)-N-(3,4-difluorophenyl)cyclopropane-1,1-dicarboxamide
- 4-methoxybenzyl 1-((4-(4-(1-(phenylcarbamoyl)cyclopropanecarboxamido)-2-fluoro-phenoxy)-6-methoxyquinolin-7-yloxy)methyl)cyclopropylcarbamate
- N-(4-(7-((1-aminocyclopropyl)methoxy)-6-methoxyquinolin-4-yloxy)-2-fluorophenyl)-N-(phenyl)cyclopropane-1,1-dicarboxamide
- N-(phenyl)-N-(2-fluoro-4-(6-methoxy-7-((1-(tetrahydro-2H-pyran-4-ylamino)cyclopropyl)-methoxy)quinolin-4-yloxy)phenyl)cyclopropane-1,1-dicarboxamide
- N-(4-(7-((1-(cyclohexylamino)cyclopropyl)methoxy)-6-methoxyquinolin-4-yloxy)-2-fluoro-phenyl)-N-(phenyl)cyclopropane-1,1-dicarboxamide
- N-(4-(7-((1-(cyclopropylmethylamino)cyclopropyl)methoxy)-6-methoxyquinolin-4-yloxy)-2-fluorophenyl)-N-(phenyl)cyclopropane-1,1-dicarboxamide
- N-(4-(7-((1-(cyclopentylamino)cyclopropyl)methoxy)-6-methoxyquinolin-4-yloxy)-2-fluoro-phenyl)-N-(phenyl)cyclopropane-1,1-dicarboxamide or a pharmaceutically acceptable salt thereof.

6. A compound according to any one of claim 1 to 5 that a pharmaceutical acceptable salt is HCl salt or tartaric acid salt.

7. A method of treating a neoplastic or proliferative disorder, especially those caused by excess or inappropriate tyrosine kinases; to a subject in need thereof by administering an effective amount of a compound in any one of claim 1-6.

* * * * *